US009632029B2

(12) United States Patent
Ikami

(10) Patent No.: US 9,632,029 B2
(45) Date of Patent: Apr. 25, 2017

(54) FLUORESCENCE IMAGING APPARATUS AND LIGHT SOURCE UNIT THEREOF

(71) Applicant: FUJIFILM Corporation, Tokyo (JP)

(72) Inventor: Seishi Ikami, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 86 days.

(21) Appl. No.: 14/632,391

(22) Filed: Feb. 26, 2015

(65) Prior Publication Data
US 2015/0241003 A1 Aug. 27, 2015

(30) Foreign Application Priority Data

Feb. 27, 2014 (JP) .................. 2014-036855

(51) Int. Cl.
*G01N 21/64* (2006.01)
*G01J 3/44* (2006.01)
(Continued)

(52) U.S. Cl.
CPC .......... *G01N 21/6456* (2013.01); *F21K 9/20* (2016.08); *G01J 3/10* (2013.01); *G01J 3/4406* (2013.01); *F21Y 2113/13* (2016.08); *F21Y 2115/10* (2016.08); *G01N 2021/6419* (2013.01); *G01N 2021/6421* (2013.01); *G01N 2021/6463* (2013.01); *G01N 2201/0627* (2013.01)

(58) Field of Classification Search
CPC ....... G01J 3/10; G01J 3/4406; G01N 21/6458
See application file for complete search history.

(56) References Cited

U.S. PATENT DOCUMENTS 8,658,989 B2 2/2014 Ikami et al.
2012/0063133 A1* 3/2012 Takeuchi .......... G02F 1/133603
362/235

(Continued)

FOREIGN PATENT DOCUMENTS

JP 2010-91456 A 4/2010
JP 2011-49536 A 3/2011
(Continued)

OTHER PUBLICATIONS

Extended European Search Report, dated Jun. 25, 2015, for corresponding European Application No. 15156970.4.
(Continued)

*Primary Examiner* — Casey Bryant
(74) *Attorney, Agent, or Firm* — Birch, Stewart, Kolasch & Birch, LLP

(57) ABSTRACT

A light source unit has two or more types of emission units which apply excitation light of three colors (blue, green, and red). The emission units share a single circuit board. LEDs of the respective emission units are mounted on the circuit board. An excitation light filter, which limits a wavelength range of light to generate the excitation light, is placed in front of each LED in direction of light emission from the LED. Each emission unit has a mounting area that faces the excitation light filter. Blue light from the LED excites resin contained in the circuit board and causes harmful light. Light shielding sections provided around the mounting area prevent the harmful light from being transmitted to another emission unit through the circuit board. Each light shielding section is composed of through holes.

21 Claims, 18 Drawing Sheets

(51) Int. Cl.
*G01J 3/10* (2006.01)
*F21K 9/20* (2016.01)
*F21Y 115/10* (2016.01)
*F21Y 113/13* (2016.01)

(56) References Cited

U.S. PATENT DOCUMENTS

2012/0248989 A1* 10/2012 Ikami ................ H01L 31/02019
   315/151
2012/0298885 A1* 11/2012 Ikami ................ G01N 21/6428
   250/459.1

FOREIGN PATENT DOCUMENTS

| JP | 2012-23110 A | 2/2012 |
| JP | 2013-169408 A | 9/2013 |
| JP | 5323130 B2 | 10/2013 |

OTHER PUBLICATIONS

Japanese Office Action dated Mar. 9, 2016, issued in Japanese Patent Application No. 2014-036855.

* cited by examiner

FLUORESCENCE IMAGING APPARATUS AND LIGHT SOURCE UNIT THEREOF

CROSS-REFERENCE TO RELATED APPLICATIONS

The present application claims priority under 35 U.S.C. §119 to Japanese Patent Application No. 2014-036855, filed Feb. 27, 2014. The above application is hereby expressly incorporated by reference, in its entirety, into the present application.

BACKGROUND OF THE INVENTION

1. Field of the Invention

The present invention relates to a fluorescence imaging apparatus for taking a fluorescent image by using excitation light and a light source unit for the fluorescence imaging apparatus.

2. Description Related to the Prior Art

In fields of biochemical and molecular biological researches, fluorescence imaging apparatuses for sample analysis are known (see U.S. Pat. No. 8,658,989 (corresponding to Japanese Patent No. 5323130) and Japanese Patent Laid-Open Publication No. 2010-091456). The fluorescence imaging apparatus applies excitation light to a sample containing a fluorescent substance (or fluorescent material) and detects excited fluorescence to take a fluorescent image. The sample is, for example, a biological substance (e.g. DNA, RNA, enzyme, antibody, or antigen) or a living body of a mouse, a rat, or the like.

In a case where a biological substance is used as a sample, a fluorescent dye is added as a marker substance (marker) to the sample. The fluorescent dye generates fluorescence by the application of the excitation light. The fluorescent image is obtained by detecting the fluorescence from the fluorescent dye. The fluorescent image shows reaction and distribution of the biological substance in the sample. By analyzing the fluorescent image, isolation or identification of a gene order, expression levels of genes, or protein is performed. In a case where a living body (or living organism) is used as a sample, the excitation light is applied to the living body to take the fluorescent image. The living body has tissue containing a fluorescent substance that generates autofluorescence, or a fluorescent dye may be given as a marker to the living body. The living body is examined by analyzing the distribution of the autofluorescence or the fluorescent dye in the fluorescent image of the living body.

The fluorescence imaging apparatus comprises a light source unit and a camera section. The light source unit applies excitation light to a sample. The camera section has an image sensor that takes fluorescent images. Different fluorescent substances have different excitation wavelength ranges. A type of excitation light to be emitted from the light source unit is selected based on the excitation wavelength range of the fluorescent substance. The image sensor detects the fluorescence excited by the selected excitation light. The camera section is provided with a filter unit. For example, the filter unit allows only the fluorescence from the fluorescent substance to enter the image sensor. The light source unit described in the U.S. Pat. No. 8,658,989 comprises different types of emission units that apply different colors of excitation light. The different types of emission units have different types of light emitting elements that emit different colors of light, respectively. The light emitting element is an LED (Light Emitting Diode), for example. The light source unit of the U.S. Pat. No. 8,658,989 selectively uses the emission units of different colors. Thereby, the light source unit is easily capable of exciting different types of fluorescent substances with different excitation wavelength ranges.

The Japanese Patent Laid-Open Publication No. 2010-091456 describes a light source unit comprising three types of emission units that emit excitation light of three colors in a blue (B) region, a green (G) region, and a red (R) region. A "B emission unit" has a B-LED that emits blue light and a "B excitation light filter" placed in front of the B-LED. A "G emission unit" has a G-LED that emits green light and a "G excitation light filter" placed in front of the G-LED. An "R emission unit" has an R-LED that emits red light and an "R excitation light filter" placed in front of the R-LED.

The excitation wavelength range of the fluorescent substance is narrower than the emission wavelength range of the LED of each color. The excitation light filter of each color cuts wavelengths of light from the LED of each color outside the excitation wavelength range. Thereby the wavelength range of the light to be applied to the fluorescent substance is narrowed.

A light component outside the excitation wavelength range applied to the fluorescent substance does not contribute to the excitation of the fluorescent substance, and what's worse, increases the brightness level of the background in the fluorescent image. As a result, the contrast between the fluorescence and the background is reduced. Since the excitation light filter removes the light component outside the excitation wavelength range, the increase in the brightness level of the background is suppressed and excellent distinguishability of the fluorescence in the fluorescent image is ensured.

To reduce the cost of the light source unit, the inventor is examining to mount different types of LEDs (B-LED, G-LED, R-LED, and the like) in one-dimensional or two-dimensional arrangement on a single circuit board. In other words, the single circuit board is shared by the emission units of different colors. A front cover is attached to the front face of the circuit board. For example, the front cover is also shared by the emission units of different colors. The front cover is provided with emission windows through which different colors (B, G, and R) of excitation light is applied. The emission window of each color is composed of the excitation light filter of the corresponding color (B, G, or R) and a window frame into which the excitation light filter is fit.

In a case where the single circuit board is shared by the different types of emission units, the circuit board causes harmful light that is harmful to the fluorescent image. The harmful light is imaged and appears in the fluorescent image. To be more specific, the circuit board is a printed circuit board in which a wiring pattern and the like are printed on a substrate. For example, resin (e.g. glass epoxy) with light transmitting property is used as the substrate. A fluorescent component contained the resin (glass epoxy) is excited by the blue light from the B-LED, and thereby generates green fluorescence (resin-derived fluorescence) derived from the resin. The green resin-derived fluorescence is imaged and appears as the harmful light in the fluorescent image.

In the B emission unit, the B excitation light filter is placed in front of the B-LED. Even if the green resin-derived fluorescence occurs, the green resin-derived fluorescence is cut by the B excitation light filter and does not go out of the B excitation light filter. However, the circuit board has the light transmitting property. In a case where the single circuit board is shared by the different types of emission units, the green resin-derived fluorescence is transmitted to, for example, the G emission unit adjacent to the B emission unit. In a case where the wavelengths of the green resin-derived fluorescence are included in the transmission wavelength range of the G excitation light filter, the green resin-derived fluorescence is released through the G excitation light filter.

In a case where the fluorescent substance excited by the B excitation light generates the fluorescence of a green region, the wavelengths of both the green resin-derived fluorescence and the green fluorescence from the fluorescent substance are within the same green region. For example, in a case where the filter unit of the camera section passes both the green resin-derived fluorescence and the green fluorescence from the fluorescent substance, both the green fluorescences enter the image sensor 22. Thus, the resin-derived fluorescence is imaged and appears in the fluorescent image. In the fluorescent image, the green resin-derived fluorescence increases the brightness level of the background and reduces the contrast between the background and the green fluorescence from the fluorescent substance. Thus, the green resin-derived fluorescence is harmful to the fluorescent image.

SUMMARY OF THE INVENTION

An object of the present invention is to provide a fluorescence imaging apparatus capable of preventing harmful light, which is caused by a circuit board of a light source unit, from being imaged in a fluorescent image and a light source unit for use in a fluorescence imaging apparatus.

In order to achieve the above and other objects, the fluorescence imaging apparatus according to the present invention comprises a light source unit for applying different types of excitation light to a sample for the purpose of exciting the fluorescent substance. The different types of excitation light have different wavelength ranges. The fluorescence imaging apparatus detects excited fluorescence and takes a fluorescence image. The light source unit comprises different types of emission units, a circuit board, and a light shielding section. The different types of emission units have a plurality of light emitting elements and different types of excitation light filters. Each emission unit has at least one of the light emitting elements and one of the excitation light filters. Each excitation light filter is disposed in front of at least one light emitting element in a direction of applying light and limits a wavelength range of the light from the light emitting element. Thereby the different types of excitation light are applied. The circuit board has a light-transmitting substrate. The light emitting elements are mounted on the circuit board. The different types of the emission units are arranged in one or two dimensions over the circuit board and share the circuit board. The light shielding section is composed of through holes formed through the circuit board so as to prevent harmful light from being transmitted from one of the emission units through the circuit board and entering the adjacent emission unit. The adjacent emission unit and one of the emission units differ in type. The harmful light occurs due to the circuit board.

It is preferred that an inner wall of the through hole has a closed curved cross-section. It is preferred that the light shielding section is composed of a group of the through holes.

It is preferred that at least one light shielding section is disposed between the different types of emission units. It is preferred that at least one light shielding section is disposed in a boundary region between the adjacent emission units of the different types of the emission units. It is preferred that the emission unit has a mounting area on which the light emitting element is mounted. The mounting area is provided on the circuit board and faces the excitation light filter. The light shielding sections may be arranged around the mounting area.

It is preferred that the emission unit has a mounting area on which the light emitting element is mounted. The mounting area is provided on the circuit board and faces the excitation light filter. It is preferred that the length of the through hole is less than or equal to a width of the mounting area. It is preferred that an area of the through hole is less than or equal to an area of the light emitting element.

It is preferred that a coating which reflects or absorbs the harmful light is applied to the inner wall of the through hole. It is preferred that the coating is conductive plating.

It is preferred that a shape of the through hole is any of polygon, circle, and oval shape. It is preferred that the light emitting element is an LED. It is preferred that the through hole allows insertion of a terminal of a component mounted on the circuit board.

It is preferred that at least one through hole is disposed in a linear path of the harmful light occurring in one of the different types of emission units and traveling linearly toward the another emission unit. It is preferred that the through holes are in a staggered arrangement.

It is preferred that a material of the circuit board is glass epoxy. It is preferred that the excitation light filters include a green excitation light filter for generating green excitation light having a wavelength range of a green region.

The light source unit according to the present invention is used in a fluorescence imaging apparatus, which excites a fluorescent substance contained in a sample, detects excited fluorescence, and takes a fluorescent image. The light source unit applies different types of excitation light to the sample for the purpose of exciting the fluorescent substance. The different types of excitation light have different wavelength ranges. The light source unit comprises different types of emission units, a circuit board, and a light shielding section. The different types of emission units have a plurality of light emitting elements and different types of excitation light filters. Each emission unit has at least one of the light emitting elements and one of the excitation light filters. Each excitation light filter is disposed in front of at least one light emitting element in a direction of applying light and limits a wavelength range of the light from at least one light emitting element. Thereby the different types of excitation light are applied. The circuit board has a light-transmitting substrate. The light emitting elements are mounted on the circuit board. The emission units are arranged in one or two dimensions over the circuit board and share the circuit board. The light shielding section is composed of through holes formed through the circuit board so as to prevent harmful light from being transmitted from one of the emission units through the circuit board and entering the adjacent emission unit. The adjacent emission unit and one of the emission units differ in type. The harmful light occurs due to the circuit board.

The fluorescence imaging apparatus comprises a light shielding section composed of through holes that penetrate the circuit board. The light shielding section prevents harmful light, which occurs due to the circuit board, from being transmitted from one type of emission unit to a different type of emission unit through the circuit board and entering the different type of emission unit. Thereby, the fluorescence imaging apparatus capable of preventing the harmful light from being imaged in a fluorescent image and the light source unit for use in the fluorescence imaging apparatus are provided.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS (First Embodiment)

Figure 1:
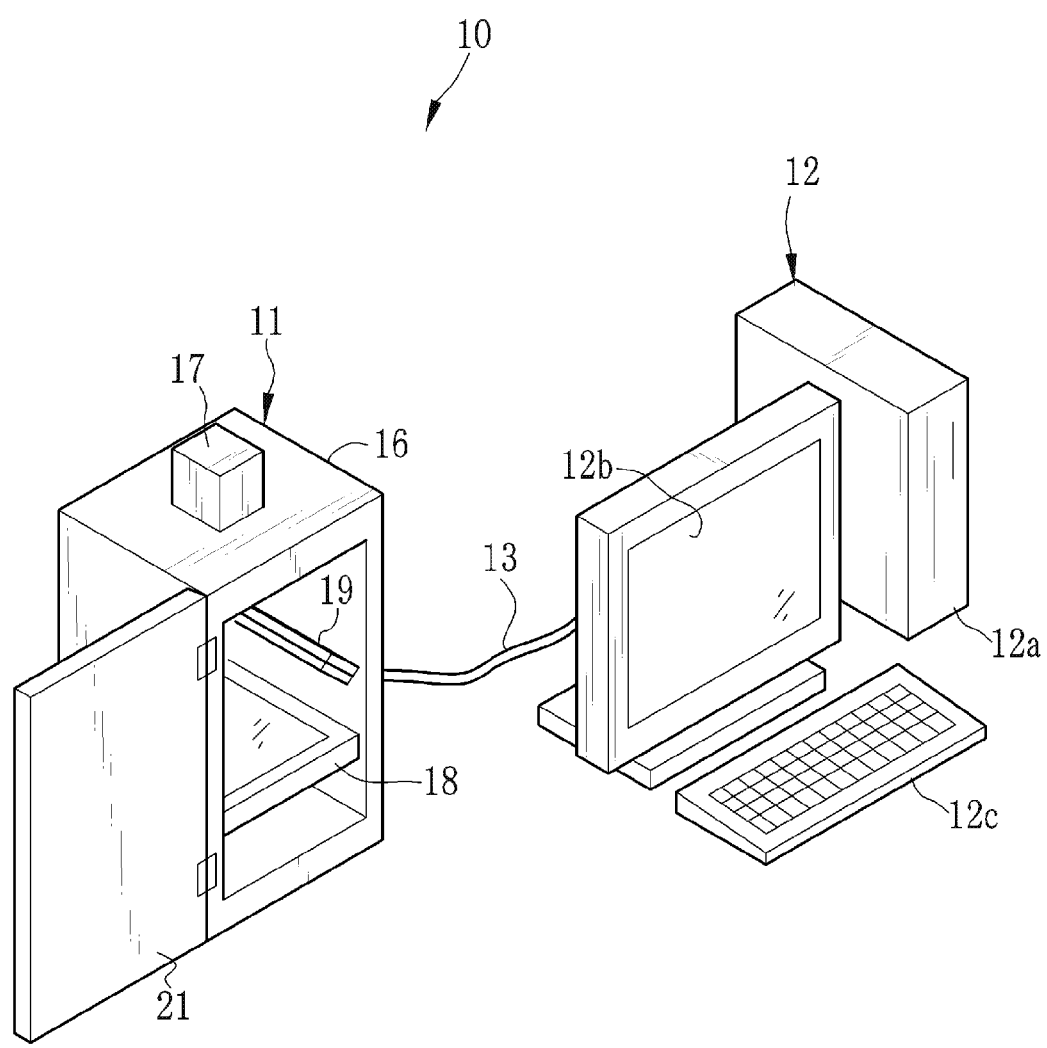
FIG. 1 is an external view of a fluorescence imaging system according to the present invention.

In FIG. 1, a fluorescence imaging system 10 comprises a fluorescence imaging apparatus 11 and an image processing device 12. The fluorescence imaging apparatus 11 applies excitation light to a sample PS that contains a fluorescent substance (or fluorescent material) and detects excited fluorescence to take a fluorescent image. The image processing device 12 performs image processing on the fluorescent image taken by the fluorescence imaging apparatus 11 and then displays the fluorescent image after the image processing. The image processing device 12 has a function to control the fluorescence imaging apparatus 11.

The image processing device 12 comprises a main body 12a (e.g. a personal computer or a work station) installed with software which contains an image processing program and a control program for controlling the fluorescence imaging apparatus 11. The image processing device 12 has a monitor 12b and an operation unit 12c. The operation unit 12c is composed of a keyboard, a mouse, and the like. The monitor 12b displays the fluorescent image, an operation screen, or the like. The operation unit 12c is used for inputting operation commands to the main body 12a through the operation screen or the like. The image processing device 12 is connected to the fluorescence imaging apparatus 11 through a cable 13 in a communicable manner.

The fluorescence imaging apparatus 11 comprises a housing 16, a camera section 17, a stage 18, and a light source unit 19. The housing 16 has a substantially rectangular-parallelepiped shape with a hollow interior. An openable and closable door 21 is provided on the front of the housing 16. The stage 18 is provided inside the housing 16. A sample PS, being a subject, is placed on the stage 18. When the door 21 is closed, the housing 16 is light-shielded. The door 21 prevents external light outside the housing 16 from entering the housing 16 or the camera section 17.

Figure 2:
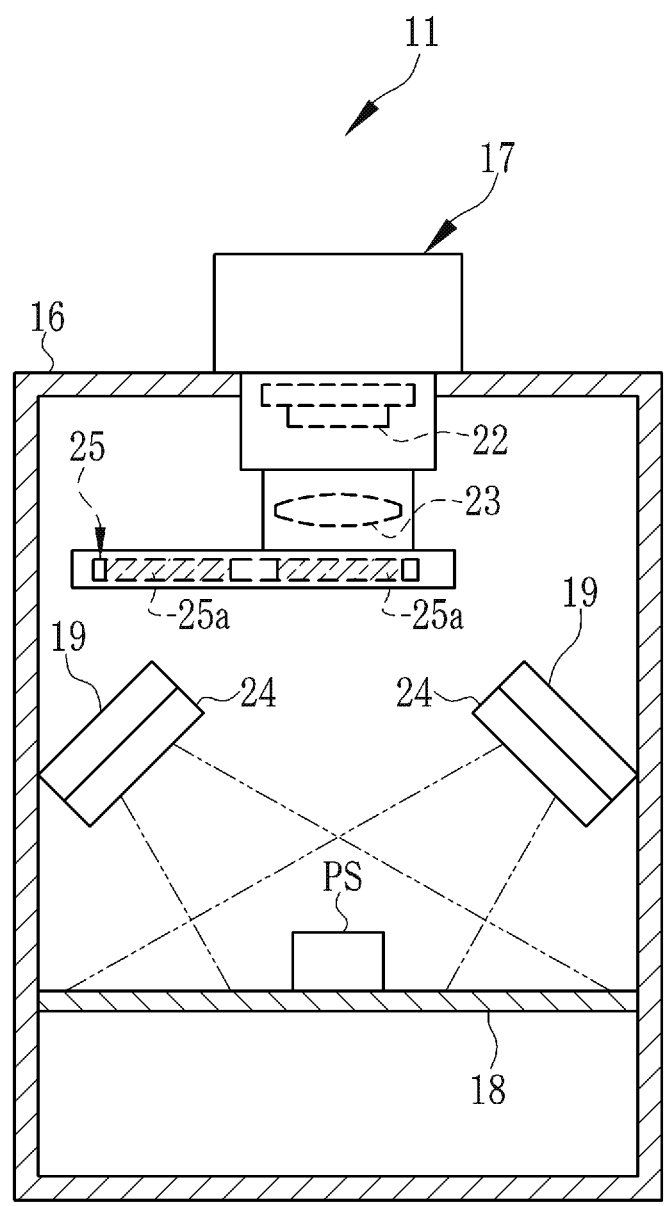
FIG. 2 is a schematic view of the fluorescence imaging apparatus.

As illustrated in FIG. 2, the camera section 17 is provided above and in an upper portion of the housing 16. A lower portion of the camera section 17 penetrates from the upper surface of the housing 16 to the inside of the housing 16. The camera section 17 detects fluorescence from the sample PS to take a fluorescent image.

The camera section 17 comprises an image sensor 22, a taking lens 23, and a filter unit 25. The image sensor 22 is an imaging device such as a CCD (Charge coupled device) image sensor or a CMOS (Complementary MOS) image sensor in which a plurality of pixels are arranged in two dimensions in a light receiving surface. The image sensor 22 is a monochrome image sensor for taking monochrome images. The taking lens 23 forms an image of the fluorescence from the sample PS, on the light receiving surface of the image sensor 22.

The filter unit 25 is placed in front of the taking lens 23. The filter unit 25 limits a wavelength range of light incident on the image sensor 22. The filter unit 25 is composed of a rotary filter, for example. The rotary filter is composed of two or more types of filters 25*a* and a rotary plate, to which the filters 25*a* are provided. The filters 25*a* differ from each other in wavelength range for transmitting light. For example, the rotary filter is provided with four types of filters 25*a*. The filters 25*a* are selectively inserted into an incident light path of the image sensor 22. The filter unit 25 is driven by a motor. The filters 25*a* are switched by rotating the filter unit 25. The filter 25*a* is an excitation light cutting filter, for example. The excitation light cutting filter cuts the excitation light applied to the sample PS and light from the sample PS other than the fluorescence. Different types of samples PS have different excitation wavelength ranges. Fluorescences from the different types of samples PS have different wavelength ranges. Light transmitting properties of the filters 25*a* are determined or selected as appropriate in accordance with the type of the sample PS. The different types of filters 25*a* are provided to correspond to the different wavelength ranges of the excitation light and the fluorescence.

In this example, the filter unit 25 is placed in front of the taking lens 23. Note that the filter unit 25 may be placed between the taking lens 23 and the image sensor 22. In a case where the taking lens 23 is composed of two or more lenses, the filter unit 25 may be placed between the lenses.

A cooling unit (not shown) is provided behind the image sensor 22. The cooling unit cools the image sensor 22 to suppress temperature rise. For example, a Peltier device is used as the cooling unit. Temperature rise increases dark current noise of the image sensor 22. Cooling the image sensor 22 with the cooling unit reduces the dark current noise.

Figure 3:
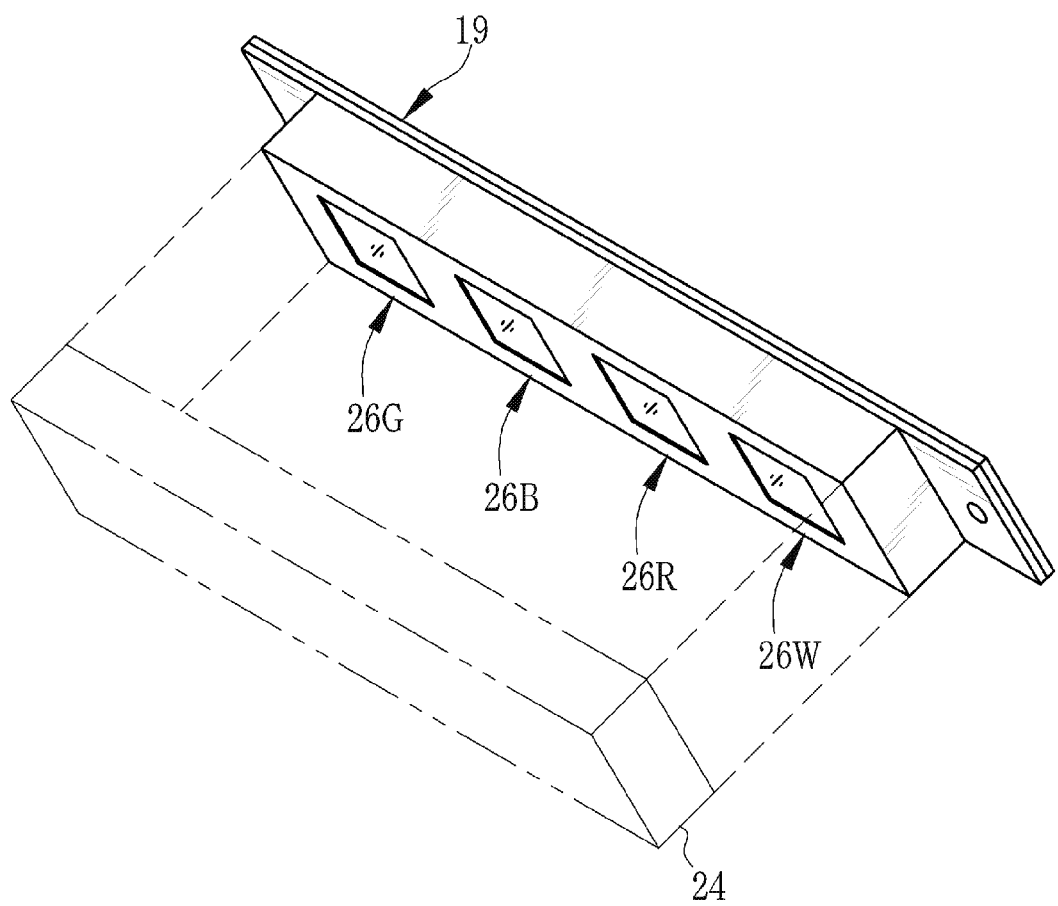
FIG. 3 is an explanatory view of a light source unit.

Obliquely above the stage 18, the two light source units 19 are opposed in a left-right direction. As illustrated in FIG. 3, each of the light source units 19 comprises a G emission unit (or simply referred to as the emission unit) 26G for applying G (green) excitation light, a B emission unit (or simply referred to as the emission unit) 26B for applying B (blue) excitation light, and an R emission unit (or simply referred to as the emission unit) 26R for applying R (red) excitation light. In addition, the light source unit 19 has a W emission unit (or simply referred to as the emission unit) 26W for applying white light that is used as illumination light. The emission units 26 are arranged in a line (one dimension). The light source unit 19 has a long thin shape as a whole. Each light source unit 19 is disposed such that the lengthwise direction of the light source unit 19 and one side of the stage 18 are substantially parallel.

An optical unit 24 is placed in front of each of the light source units 19. The optical unit 24 broadens an irradiation area of the excitation light or the illumination light from the emission unit 26, or reduces unevenness in light distribution in the irradiation area. The optical unit 24 may be composed of a collimator lens for collimating light or diffusion plate for diffusing light, for example. The start and the end of the operation of the camera section 17, turning on and off the light source unit 19, switching between the excitation light and the illumination light, and the like are controlled by control signals inputted from the image processing device 12.

Figure 4:
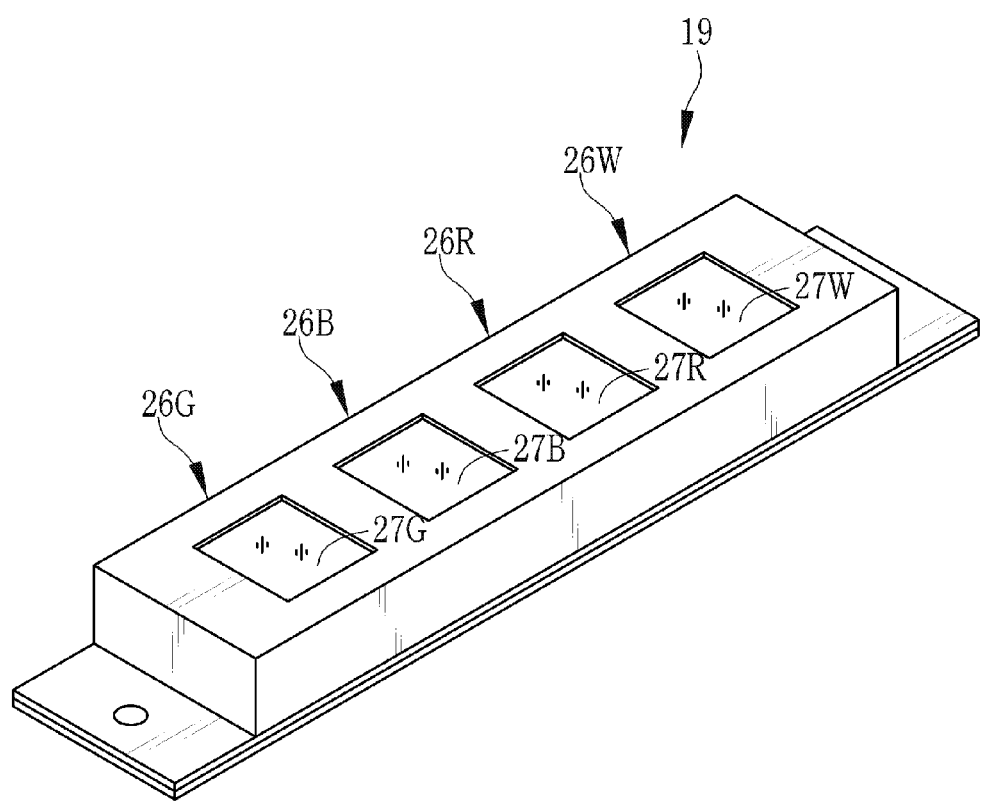
FIG. 4 is a perspective view of the light source unit.

As illustrated in FIG. 4, the four types of emission units 26G, 26B, 26R, and 26W have their respective emission windows 27G, 27B, 27R, and 27W. The different colors of excitation light correspond to the excitation wavelength ranges of the fluorescent substances, respectively. The light source unit 19 is capable of selectively applying the different colors of excitation light. The different colors of excitation light are selectively used in accordance with the fluorescent substance contained in the sample PS, being the subject of analysis. The emission unit 26W that applies the illumination light (white light) may be turned on individually or together with the emission unit 26G, 26B, or 26R.

Figure 5:
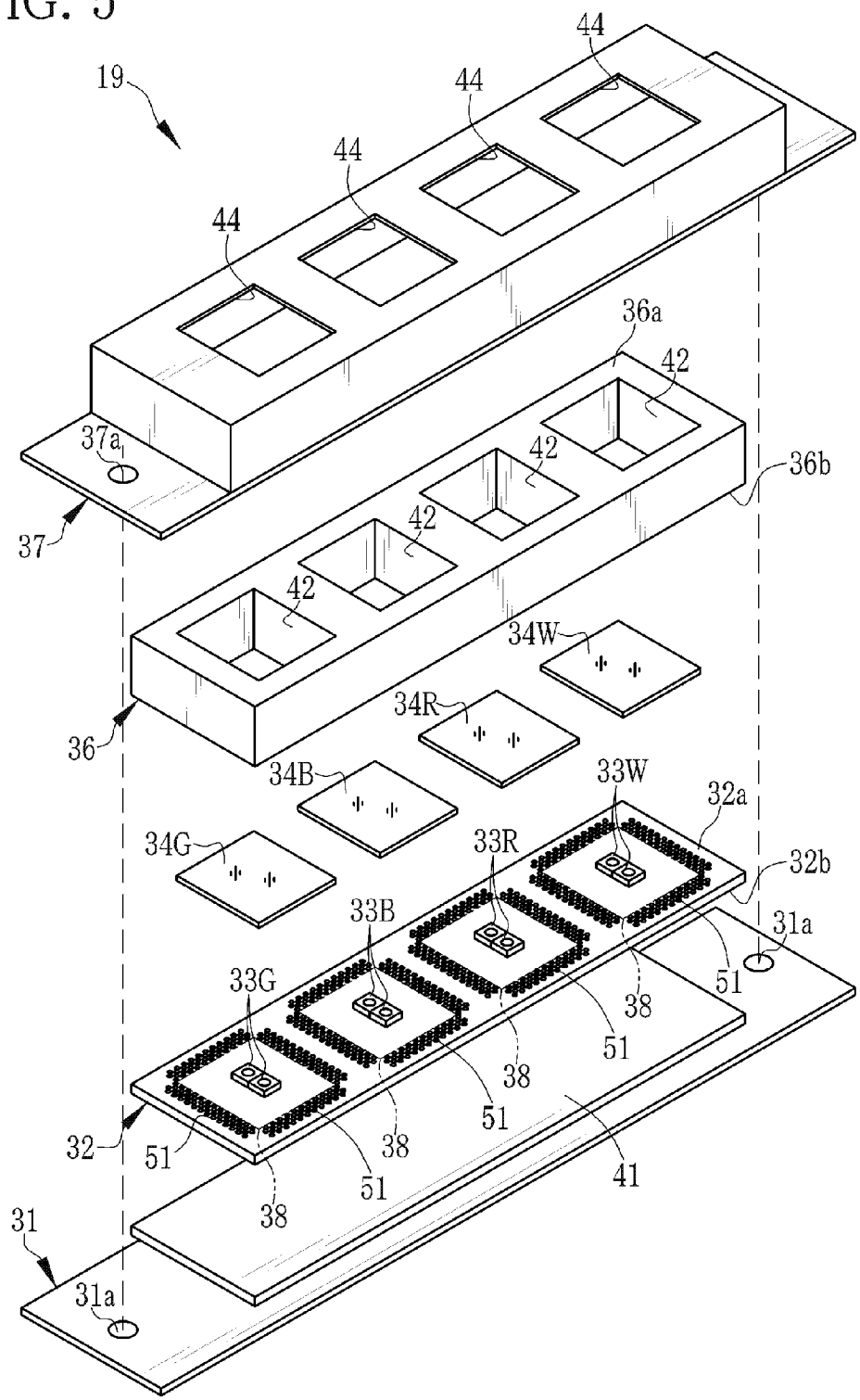
FIG. 5 is an exploded perspective view of the light source unit.
Figure 6:
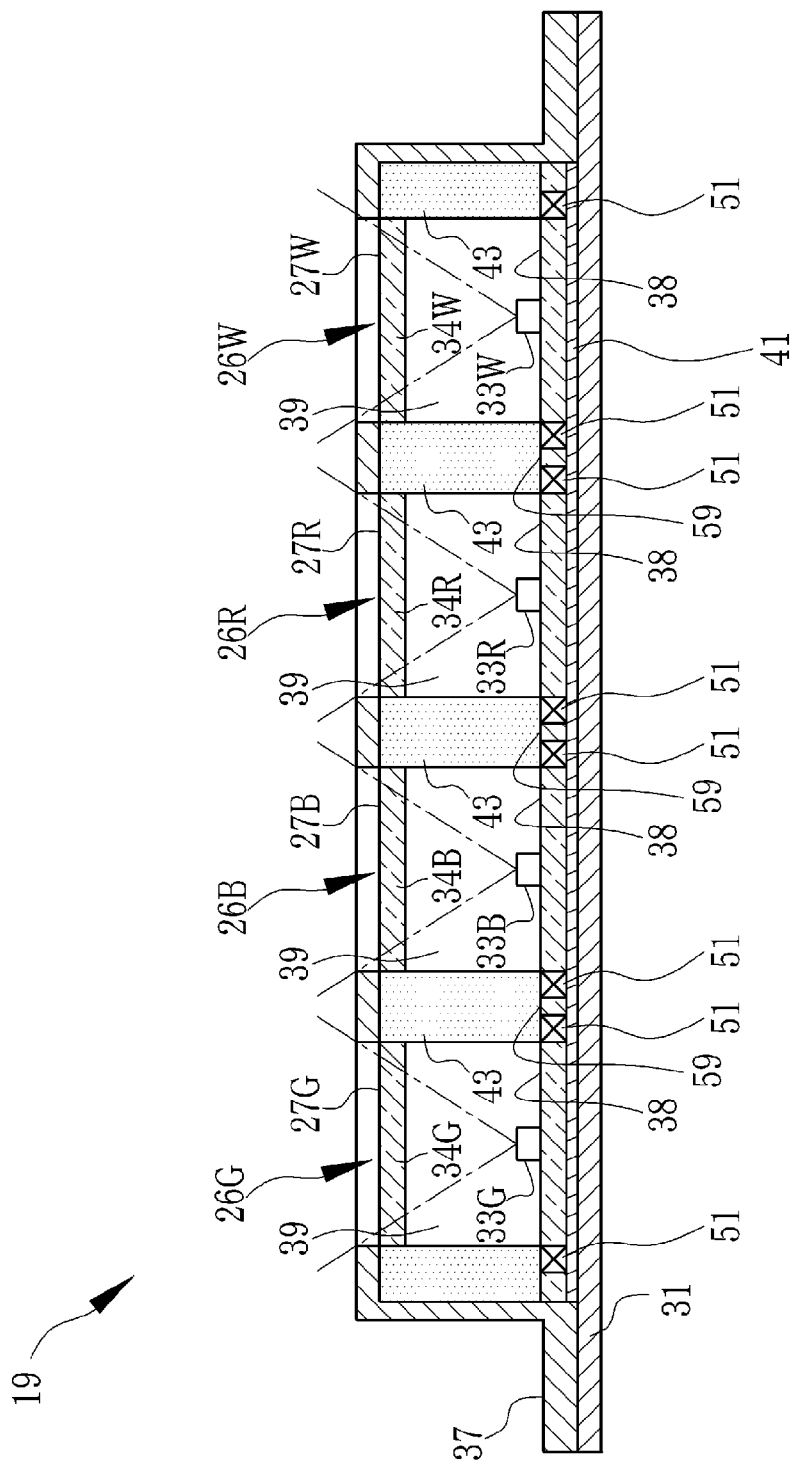
FIG. 6 is a cross-sectional view of the light source unit.

As illustrated in FIGS. 5 and 6, the light source unit 19 is composed of a chassis 31, a circuit board 32, a G LED 33G, a B LED 33B, an R LED 33R, and a W LED 33W of respective colors G (green), B (blue), R (red), and W (white), filters 34G, 34B, 34R, and 34W of the respective colors G, B, R, and W, a window frame block 36 for attaching the filters 34G, 34B, 34R, 34W, and a front cover 37. Here, a character "B", "G", "R", or "W" that specifies a color is added as necessary to the numeral of the emission unit, the emission window, the LED, the filter, or the like to distinguish the color thereof. In a case where it is unnecessary to distinguish the colors, the character specifying the color is omitted. The emission unit 26, the emission window 27, the LED 33, or the filter 34 is referred to as it is, without the character specifying the color.

The filters 34G, 34B, and 34R correspond to the G-LED 33G, the B-LED 33B, and the R-LED 33R. Each of the filters 34G, 34B, and 34R is used for generating excitation light that excites a fluorescent substance. The filters 34G, 34B, and 34R have light transmitting properties to transmit parts of the wavelength ranges of the light from the LEDs 33G, 33B, and 33R, respectively. The wavelength range of the light from each of the G-LED 33G, the B-LED 33B, and the R-LED 33R is broader than the excitation wavelength range of the fluorescent substance. In a case where the light components outside the excitation wavelength range is applied to the fluorescent substance, the light components do not contribute the excitation of fluorescence. What's worse, the light components outside the excitation wavelength range increase the brightness level of the background of the fluorescent image, thereby reducing the distinguishability of the fluorescence in the fluorescent image. The filters 34G, 34B, and 34R cut the wavelengths of the light from the G-LED 33G, B-LED 33B, and R-LED 33R outside the excitation wavelength ranges, respectively. Thereby, the wavelength range of the light from each of the G-LED 33G, the B-LED 33B, and the R-LED 33R is narrowed. Thus, the excitation light that corresponds to the excitation wavelength range of the fluorescent substance is generated.

Of the white light from the W-LED 33W, the filter 34W cuts wavelength components (e.g. infrared light and UV light) which are unnecessary for the illumination light. Note that instead of the filter 34W, a light transmission plate with no filter function may be used for the W emission unit 26W in a case where a filter function is unnecessary.

The chassis 31 is a flat metal plate and supports a back surface 32*b* side of the circuit board 32. A screw hole 31*a* is provided on each end of the chassis 31 in the lengthwise direction. The screw holes 31*a* are used for fastening the front cover 37 to the chassis 31, and the light source unit 19 to the housing 16.

The circuit board 32 is a substrate on which the LEDs 33 of the respective colors are mounted. The circuit board 32 is formed with wiring patterns and driver circuits for supplying drive currents to the LEDs 33. The circuit board 32 has a plate shape, and the LEDs 33 of the respective colors are mounted on the plate-shaped circuit board 32. For example, the circuit board 32 is a printed circuit board, being a substrate 32*c* (see FIG. 11) printed with a wiring pattern 32*d* (see FIG. 11), and the like. The substrate 32*c* is made from resin such as glass epoxy, for example, and has the light transmitting property. Amounting area 38 of each LED 33 is provided on a surface 32*a* of the circuit board 32. The mounting areas 38 correspond to the respective colors of the LEDs 33. The mounting areas 38 face the respective filters 34. In this example, the filter 34 has a rectangular plan shape. The mounting area 38 has a rectangular shape which corresponds to the plan shape of the filter 34. A pair of two LEDs 33 of the same color (hereinafter simply referred to as the LED 33) is mounted on each mounting area 38. The mounting areas 38 corresponding to the LEDs 33 of the respective colors are arranged in a line in the lengthwise direction of the circuit board 32. Light shielding sections 51 are provided around each mounting area 38 on the circuit board 32. The light shielding section 51 will be described below.

A thermal conductive sheet 41 is provided between the chassis 31 and the circuit board 32. The thermal conductive sheet 41 conducts heat from each LED 33 to the chassis 31, to dissipate the heat.

Window frames 42 for attaching the filters 34 of the different colors are formed in the window frame block 36. The window frame 42 has a rectangular plan shape that fits with the shape of the filter 34. A top face 36a of the window frame block 36 comes in contact with the inner face of the front cover 37. A back face 36b of the window frame block 36 comes in contact with the surface 32a of the circuit board 32. The inner face of the front cover 37 is provided with a positioning member (not shown) for fixing the position of the window frame block 36. When the window frame block 36 is attached to the front cover 37, the position of the window frame block 36 relative to the front cover 37 is fixed.

The window frame 42 has a function to delimit or define the mounting area 38, which is provided on the circuit board 32. The window frame block 36 holds the filter 34 with a space between the filter 34 and the circuit board 32, and thereby functions to delimit or define a mounting space 39 formed between the mounting area 38 and the filter 34. A portion of the window frame block 36 between the adjacent window frames 42 functions as a wall 43 for separating the adjacent mounting spaces 39. In other words, the wall 43 defines a boundary between the adjacent emission units 26. The wall 43 prevents light leakage from the LED 33 into the adjacent mounting space 39 of the LED 33 of a different color. The window frame block 36 is made from elastic material, for example, rubber. The elastic material increases adherence between the back face 36b of the window frame block 36 and the surface 32a of the circuit board 32. As a result, the effect of preventing the light leakage into the adjacent mounting space 39 is further improved.

The front cover 37 covers the circuit board 32 and the window frame block 36, which are attached to the chassis 31. The front cover 37 is provided with screw holes 37a that correspond to the respective screw holes 31a of the chassis 31. The front cover 37 is formed with exposure openings 44 in positions corresponding to the respective window frames 42 of the window frame block 36. The exposure openings 44 expose the filters 34, which are attached to the window frames 42, respectively, to the outside.

Each emission window 27 is composed of the filter 34 of the corresponding color, the window frame 42, and the exposure opening 44. To be more specific, the G emission window 27G for applying the G excitation light from the G-LED 33G is composed of the filter 34G, the window frame 42, and the exposure opening 44. The B emission window 27B for applying the B excitation light from the B-LED 33B is composed of the filter 34B, the window frame 42, and the exposure opening 44. The R emission window 27R and the W emission window 27W are composed in like manner.

Each emission unit 26 is composed of the emission window 27 of the corresponding color, the LED 33 of the corresponding color, and the mounting space 39 that includes the mounting area 38. The G emission unit 26G is composed of the G emission window 27G, the G-LED 33G, and the mounting space 39 of the G-LED 33G. The B emission unit 26B is composed of the B emission window 27B, the B-LED 33B, and the mounting space 39 of the B-LED 33B. Each of the R emission unit 26R and the W emission unit 26W is composed in like manner.

Figure 7:
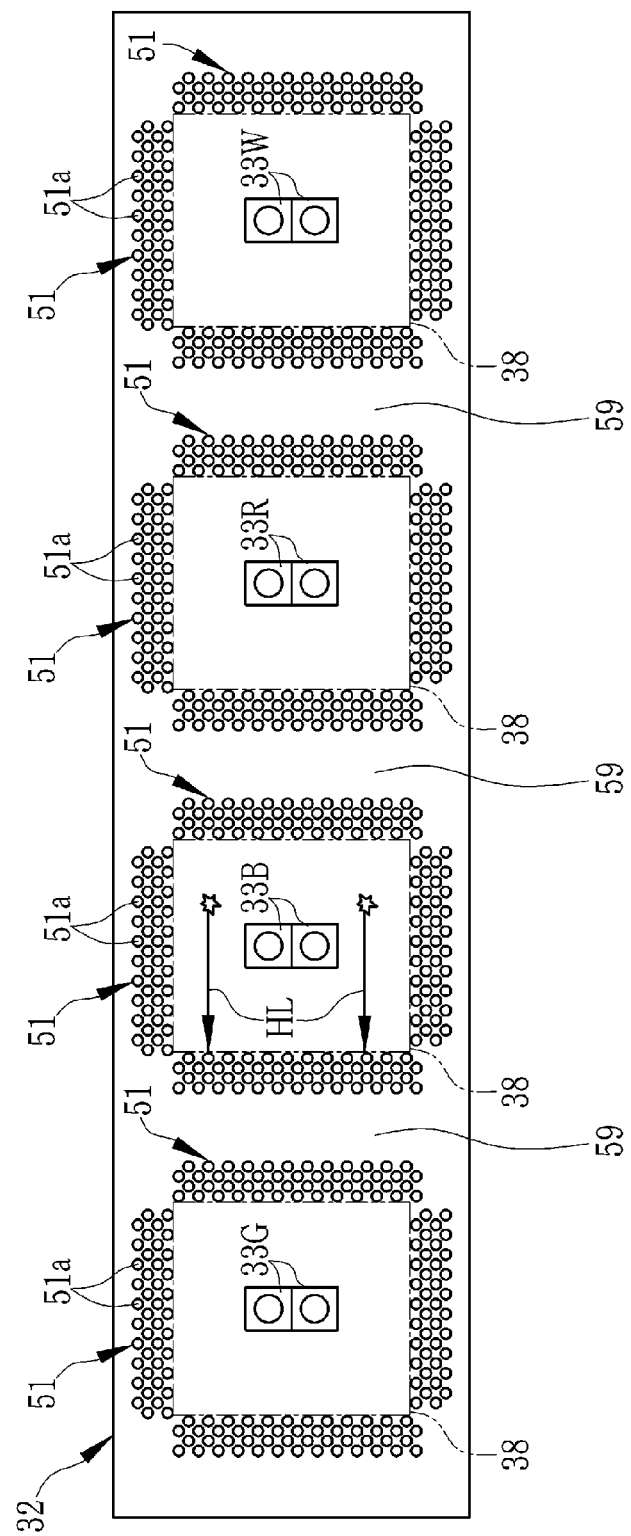
FIG. 7 is a plan view of a circuit board.

As illustrated in FIG. 7, the circuit board 32 is provided with the light shielding sections 51 surrounding each mounting area 38. To be more specific, the light shielding section 51 is provided to each side of each square-shaped mounting area 38. Thereby the light shielding sections 51 are disposed in a boundary region 59 between the adjacent emission units 26 of different types (colors). The boundary region 59 refers to an area between the mounting areas 38 of the adjacent emission units 26. In this example, the entire boundary region 59 faces the wall 43 of the window frame block 36 (see FIG. 6). As illustrated with arrows (see FIG. 7) in the mounting area 38 of the B-LED 33B, the light shielding section 51 prevents the harmful light HL, which is caused by the circuit board 32, from being transmitted to another mounting area 38 through the circuit board 32.

As described in this example, in the case where the circuit board 32 is a resin substrate made from the glass epoxy, the blue light from the B-LED 33B excites a fluorescent component in the resin and generates green fluorescence (resin-derived fluorescence). In this example, the harmful light HL refers to the green resin-derived fluorescence.

In the case where the harmful light HL is the green fluorescence, the harmful light HL from the B emission unit 26B is cut by the filter 34B, so that the harmful light HL is not emitted from the B emission unit 26B. However, the circuit board 32 has the light transmitting property. In the case where two or more emission units 26 share the single circuit board 32 as described in this example, the resin-derived harmful light HL may be transmitted from the emission unit 26B to the adjacent emission unit 26G, for example, and enter the mounting area 38 and the mounting space 39 of the emission unit 26G. In the case where the wavelength range of the harmful light HL partially overlaps the transmission wavelength range of the filter 34G, the harmful light HL which has entered the mounting space 39 of the emission unit 26G passes through the filter 34G and is released from the emission unit 26G.

In the case where the B-LED 33B is turned on and the emission unit 26B applies the B excitation light to the sample PS, it is preferred that the fluorescence from the fluorescent substance contained in the sample PS, excited by the B excitation light, has good contrast in the fluorescent image. In case the harmful light HL appears in the fluorescent image, the harmful light HL reduces the contrast in the fluorescent image and becomes noise to the fluorescence derived from the fluorescent substance.

Figure 8:
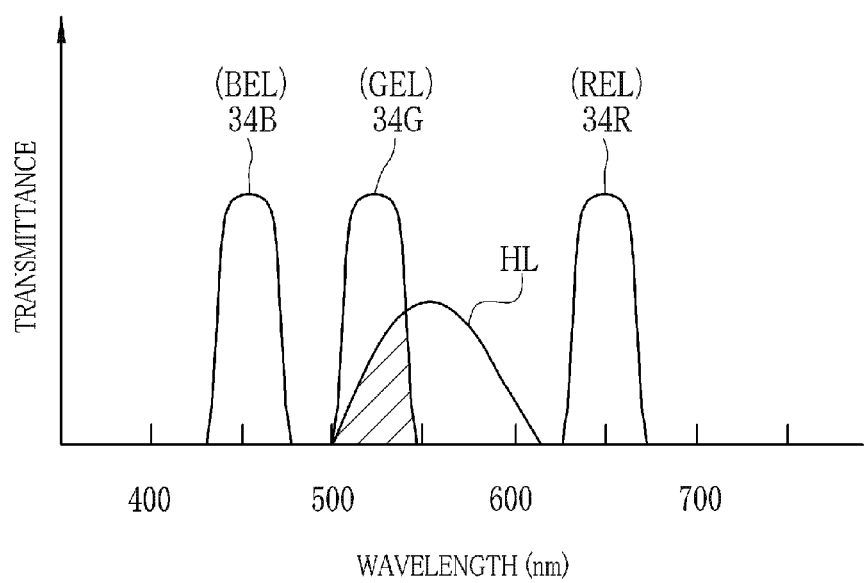
FIG. 8 is an explanatory view illustrating light transmitting properties of excitation light filters.

Specific descriptions are as follows. The filters 34B, 34G, and 34R have light transmitting properties illustrated in FIG. 8 by way of example. In this case, the filters 34B, 34G, and 34R generate B excitation light BEL, G excitation light GEL, and R excitation light REL, respectively. For example, the center wavelength of the B excitation light BEL is 470 nm; the center wavelength of the G excitation light GEL is 520 nm; the center wavelength of the R excitation light REL is 650 nm. The harmful light HL is the green light having the wavelength range of approximately 500 to 600 nm, for example. As illustrated with a hatch pattern in FIG. 8, the wavelength range of the harmful light HL partially overlaps the transmission wavelength range of the filter 34G. In a case where the harmful light HL enters the emission unit 26G, a part of the harmful light HL passes through the filter 34G for generating the G excitation light GEL and is released from the emission unit 26G.

Figure 9:
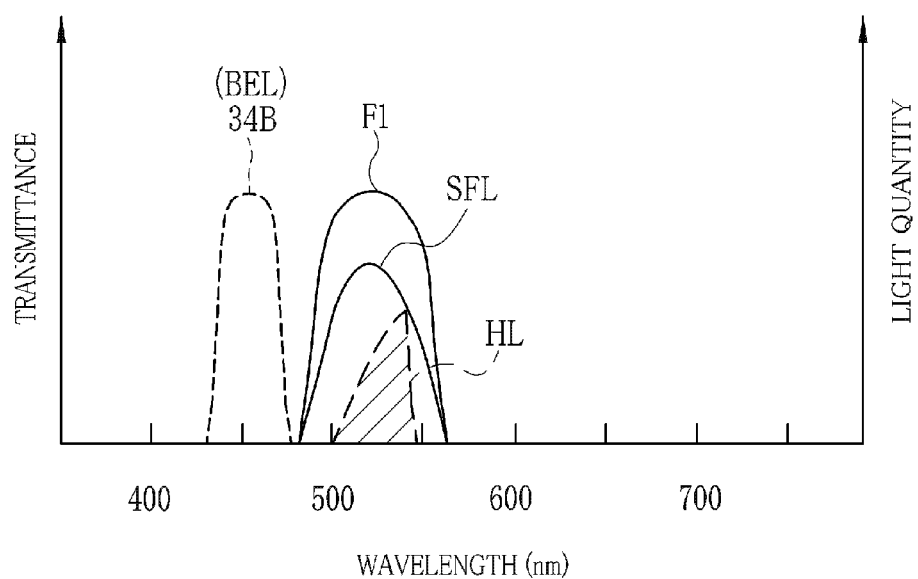
FIG. 9 is an explanatory view illustrating light transmitting properties of a filter unit of a camera section and wavelength ranges of fluorescence from a fluorescent substance and harmful light.

In FIG. 9, fluorescence SFL is emitted from the fluorescent substance excited by the B excitation light BEL. The fluorescence SFL is derived from the fluorescent substance. A center wavelength of the fluorescence SFL is 520 nm, for example. To detect the fluorescence SFL, the filter 25a having the light transmitting property corresponding to the wavelength range of the fluorescence SFL is selected from the filter unit 25 (see FIG. 2). In FIG. 9, "F1" denotes the light transmitting property of the filter 25a, which is selected to detect the fluorescence SFL. The filter 25a having the light transmitting property F1 limits the wavelength range of the light incident on the image sensor 22 and cuts the B excitation light BEL.

However, the wavelength range of the fluorescence SFL partially overlaps that of the harmful light HL passed through the filter 34G, so that both the harmful light HL released from the emission unit 26G and the fluorescence SFL pass through the filter 25a having the light transmitting property F1 and then are incident on the image sensor 22. The harmful light HL which is incident on the image sensor 22 appears in the fluorescent image. In the fluorescent image, the harmful light HL increases the brightness of the background of the fluorescent image. As a result, the harmful light HL reduces the contrast (the contrast between the fluorescence SFL and the background) in the fluorescent image.

Figure 10:
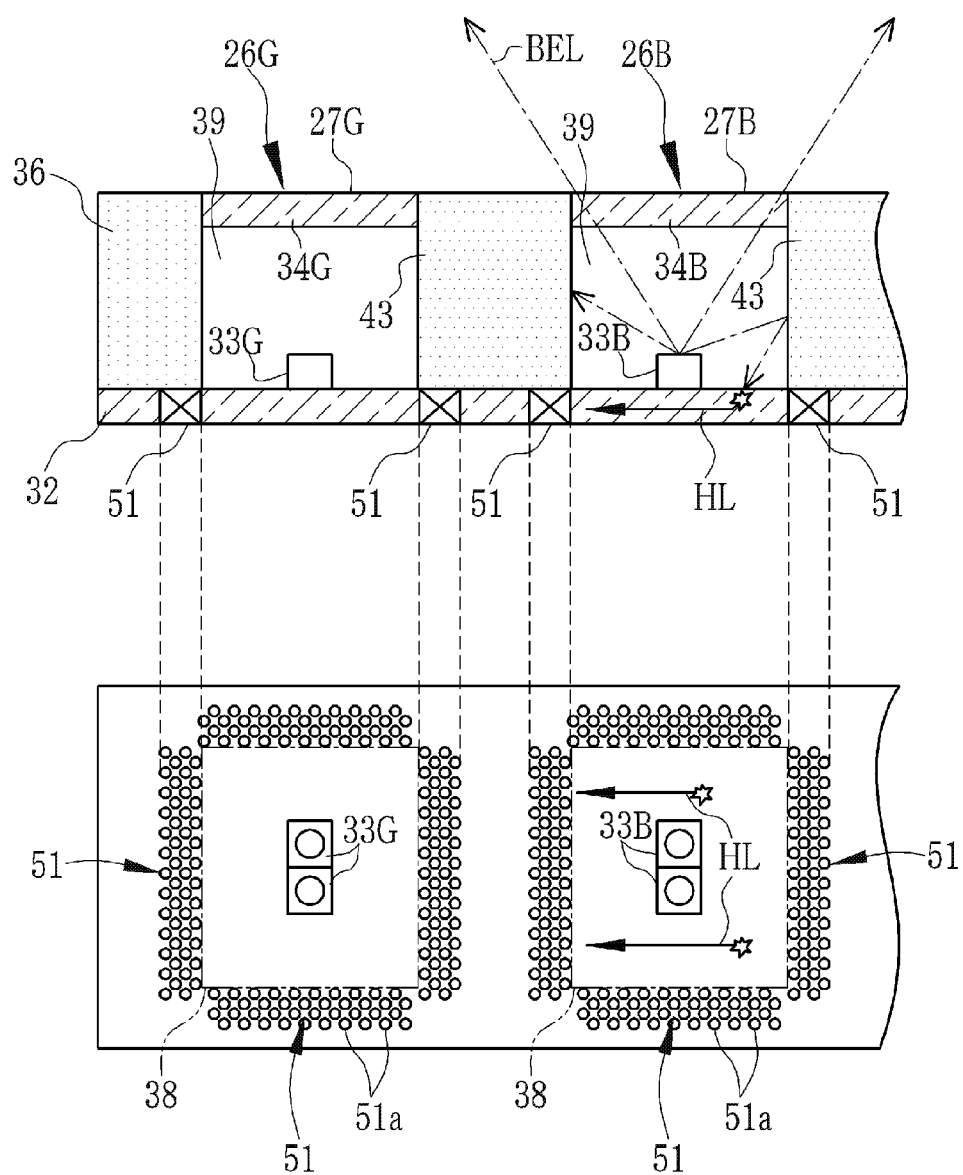
FIG. 10 is a functional explanatory view of a light shielding section.

As illustrated in FIG. 10, the light shielding section 51 prevents the harmful light HL generated in the mounting area 38 of the B emission unit 26B from being transmitted to the adjacent G emission unit 26G through the circuit board 32. Thereby the light shielding section 51 prevents the harmful light HL from entering the mounting space 39 of the G emission unit 26G. As described above, the light shielding sections 51 are provided to surround the mounting area 38. More specifically, the four light shielding sections 51 are provided to the four respective sides of the mounting area 38. The light shielding sections 51 are provided not only in the boundary regions 59 but also in areas other than the boundary regions 59. Thereby the harmful light HL traveling from the B emission unit 26B toward the G emission unit 26G through linear transmission and diffraction is blocked.

In this example, the light shielding sections 51 are provided not only around the mounting areas 38 of the B emission unit 26B and the G emission unit 26G but also around the mounting areas 38 of the emission units 26R and 26W. A reason for this is as follows. In this example, the green harmful light HL occurs in the B emission unit 26B. However, there are cases where the harmful light HL contains wavelength components of the blue light or the red light. The harmful light HL may not necessarily be the green light. The harmful light HL may occur in the emission unit other than the B emission unit 26B, for example, the emission unit 26G, 26R, or 26W.

The circuit board 32 is shared by the emission units 26B, 26G, 26R, and 26W, so that the harmful light occurred in one of the emission units 26 is likely to be transmitted or leaked to another emission unit 26. In the case where the wavelength range of the harmful light HL partially overlaps the transmission wavelength range of the nearby filter 34 of the emission unit 26 into which the harmful light HL is leaked, the harmful light HL is released to the outside of the light source unit 19 through the nearby filter 34. In this example, the light shielding sections 51 are provided to each of the emission units 26B, 26G, 26R, and 26W. Thereby the transmission or leakage of the harmful light HL into another emission unit 26 is prevented irrespective of the wavelengths of the harmful light HL or the location where the harmful light HL occurred.

Figure 11:
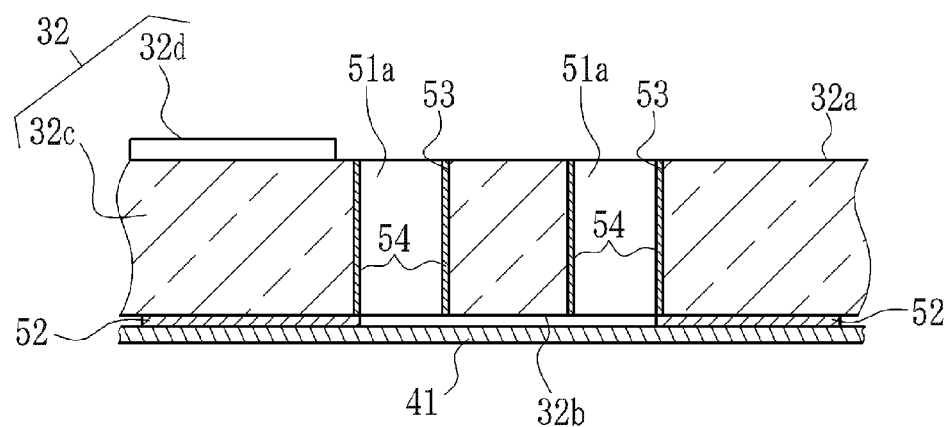
FIG. 11 is a cross-sectional view of the circuit board.

The light shielding section 51 is a group of a plurality of through holes 51a formed in the circuit board 32. The through hole 51a may be referred to as a via hole. As illustrated in FIG. 11, the through hole 51a penetrates the circuit board 32 in the thickness direction from the surface 32a to the back surface 32b of the circuit board 32. The plan shape of the through hole 51a is circular, for example. In a case where the light in the circuit board 32 is transmitted in a direction orthogonal to the thickness direction of the circuit board 32, an inner wall 53, being an interface with air, of the through hole 51a located in a traveling direction (light path) of the light causes refraction or total reflection of the light, and thereby changes the traveling direction (light path) of the light. The through hole 51a in the light path of the harmful light HL directed to the adjacent emission unit 26 changes the traveling direction of the harmful light HL. Thereby, the through holes 51a prevent all the harmful light HL from entering the adjacent emission unit 26, or at least reduce an amount of the harmful light HL entering the adjacent emission unit 26.

The light shielding section 51 provides a light shielding effect, which is an effect to prevent the harmful light HL from being transmitted to another emission unit 26. The light shielding section 51 is composed of the through holes 51a to exert the light shielding effect. For example, in a case where the light shielding section 51 is composed of concave or depressed portions with bottoms instead of the through holes 51a, the light is transmitted through the bottom portions, so that the light shielding effect cannot be achieved. For this reason, the light shielding section 51 is composed of the through holes 51a.

The light shielding sections 51 are disposed outside the mounting area 38 because emission efficiency is reduced in a case where the light shielding sections 51 are disposed inside the mounting area 38. The size of the mounting area 38 corresponds to the size of the emission window 27 including the filter 34. In the case where the through hole 51a, being the part of the light shielding section 51, is disposed inside the mounting area 38, a part of the light from the LED 33 to be emitted through the emission window 27 leaks through the through hole 51a. The light leakage results in loss of the amount of light and reduces the emission efficiency. In a case where some losses in the amount of light are acceptable, a part of the light shielding section 51 may be disposed inside the mounting area 38.

As illustrated in FIG. 11, a wiring pattern 52, which is formed from copper lines or copper foil, is provided to the back surface 32b of the circuit board 32. The through holes 51a allow insertion of a lead terminal or the like of an electrical component mounted on the circuit board 32, to be used for connection to the wiring pattern 52 formed on the back surface 32b of the circuit board 32.

It is preferred that a coating 54 is applied to the inner wall 53 of the through hole 51a. The coating 54 reflects or absorbs light including the harmful light HL. The reflection or absorption of the light by the coating 54 further improves the light shielding effect for the harmful light HL. Examples of the coatings 54 having light reflection properties include plating. Examples of the coatings 54 having light absorption properties include carbon black and black dyes. In a case where the plating is used, it is preferred to use conductive plating formed from metal material or the like. The conductive plating allows the coating 54 to exert the light reflection properties and also to serve as a part of wiring when connected to the wiring pattern 52.

Figure 12:
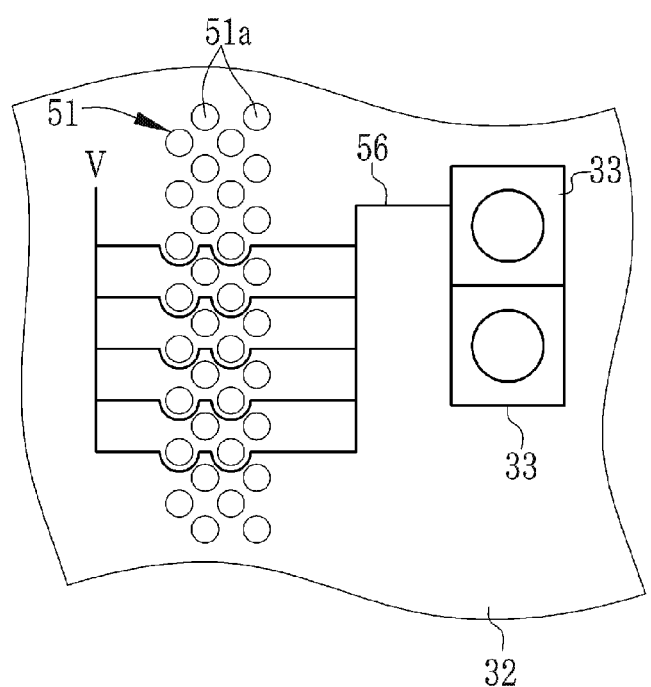
FIG. 12 an explanatory view of example in which spaces between through holes are used for wiring.

The light shielding section 51 is composed of the plurality of through holes 51a. This allows installation of wiring 56 between the through holes 51a as illustrated in FIG. 12. For example, as compared with one long hole having the area approximately the same as that of the light shielding section 51, the light shielding section 51 composed of the through holes 51a improves flexibility in installing the wiring in the circuit board 32 because the wiring 56 is installed between the through holes 51a. The drive current for the LED 33 is relatively large. The flexibility in installing the wiring allows increasing the number or the width of the wiring, reducing wiring resistance. This allows for a large current. Thus, the light shielding section 51 composed of the through holes 51a is especially effective in a case where the LED 33, which requires a large drive current, is used.

Figure 13:
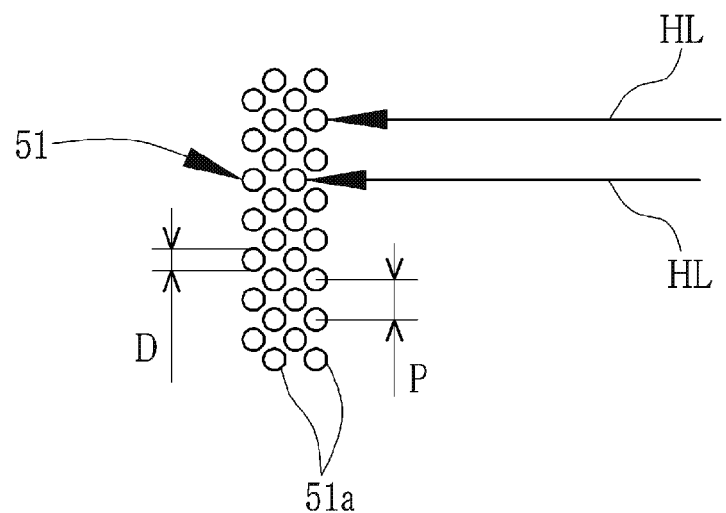
FIG. 13 is an explanatory view illustrating a staggered arrangement of the through holes.

As illustrated in FIGS. 10 and 13, the through holes 51a are in a staggered arrangement in the light shielding section 51, which corresponds to one side of the mounting area 38. To be more specific, the plurality of through holes 51a are arranged in four rows. The through holes 51a of each row is arranged at a predetermined pitch in a direction along the side. The position of the center of each through hole 51a of each row is shifted by half pitch (½ of the arrangement pitch of the through holes 51a in one row) in the row direction, relative to that of the adjacent row. The staggered arrangement increases the probability of blocking a light path as compared with a square matrix arrangement, thereby improving the light shielding effect.

To improve the light shielding effect, it is preferred to dispose at least one through hole 51a in a linear path of the harmful light HL, which occurs in one mounting area 38 and travels toward the adjacent mounting area 38. In a case where there is a remaining linear path which allows the transmission of the harmful light HL, the harmful light HL reaches the adjacent mounting area 38 without refraction or reflection, thereby reducing the light shielding effect. It is preferred to dispose the plurality of through holes 51a such that at least one through hole 51a is disposed in each linear path of the harmful light HL between the adjacent mounting areas 38 as illustrated in FIG. 13 by way of example.

Figure 14:
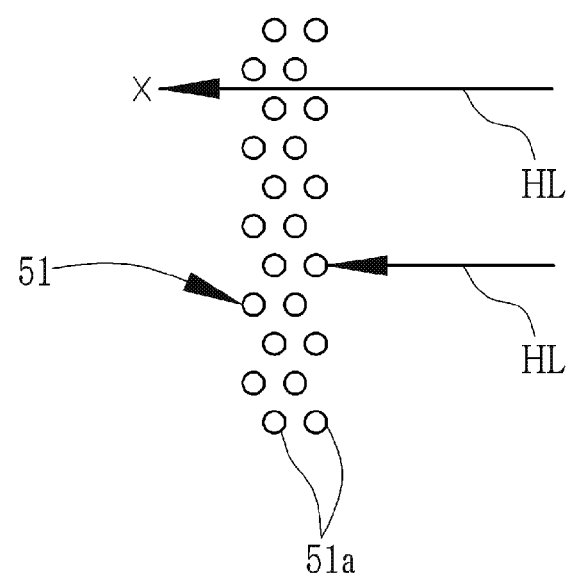
FIG. 14 is an explanatory view illustrating a staggered arrangement of through holes different from those in FIG. 14.

The arrangement pitch, the diameter, the number of rows, the length of one row, and the like of the through holes 51a are determined in consideration of the above. For example, even in the staggered arrangement, a linear path (an arrow with a mark "x" in FIG. 14) which is not blocked by the through hole 51a may occur depending on the diameter, the number of rows, and the arrangement pitch of the through holes 51a. It is preferred to set the items such as the diameter and the arrangement pitch to avoid the linear path which is not blocked by the through hole 51a. More specifically, as illustrated in FIG. 13, it is preferred that a relationship between an arrangement pitch P and a diameter D satisfies a condition $D \geq 1/2P$ where "P" denotes an arrangement pitch of the through holes 51a in a row direction parallel to one side of the mounting area 38 and "D" denotes the diameter of the through hole 51a in the row direction.

Provided that the number of the through holes 51a is not changed, strength and rigidity of the circuit board 32 are reduced in a case where the area of each through hole 51a is large. For this reason, the area of each through hole 51a is preferred to be small. More specifically, the area of each through hole 51a is preferred to be less than or equal to the area of the LED 33 as described in this example. The through holes 51a each with the area less than or equal to that of the LED 33 suppress the reduction in the strength and the rigidity of the circuit board 32 even if the arrangement density (the number of the through holes 51a per unit area) is increased by reducing the arrangement pitch of the through holes 51a.

Hereinafter, the operation of the above-described configuration is described. To take a fluorescent image of the sample PS, the sample PS is set to the stage 18 inside the housing 16. The excitation light suitable for the fluorescent substance contained in the sample PS is selected through the operation screen of the image processing device 12 with the use of the operation unit 12c. The filter 25a of the filter unit 25 is selected based on the wavelength range of the fluorescence from the fluorescent substance. The light source unit 19 turns on in response to the input of the command (which includes the command for selecting the excitation light) for turning on the light source unit 19 from the image processing device 12 to the fluorescence imaging apparatus 11. In response to the input of the command for selecting the filter 25a to the fluorescence imaging apparatus 11, the filter unit 25 is rotated and the selected filter 25a is placed in front of the image sensor 22. At the same time, the command for starting the imaging is inputted to the camera section 17, thereby allowing the image sensor 22 to start an imaging operation. The image sensor 22 outputs the images taken at a predetermined frame rate as live view images to the image processing device 12.

In a case where the B excitation light is selected, only the B-LED 33B of the light source unit 19 is turned on. The filter 34B narrows the wavelength range of the blue light from the B-LED 33B. Thereby, the B excitation light BEL (see FIG. 8) is applied to the sample PS through the B emission window 27B. The fluorescent substance contained in the sample PS emits fluorescence SFL (see FIG. 9) by the application of the B excitation light. The filter 25a with the light transmitting property F1 that corresponds to the fluorescence SFL is selected. The filter 25a cuts the B excitation light BEL while passing the fluorescence SFL, so that the fluorescence SFL enters the image sensor 22. The image sensor 22 detects the fluorescence SFL and thereby takes the fluorescent image. The fluorescent image is outputted to the image processing device 12 and then displayed on the monitor 12b.

As illustrated in FIG. 10, the blue light from the B-LED 33B excites a fluorescent component contained in the mounting area 38 of the B emission unit 26B over the circuit board 32, causing the harmful light HL. The light shielding sections 51, each of which is composed of the through holes 51a, are provided around the mounting area 38. The light shielding section 51 blocks the harmful light HL, preventing the transmission (or the leakage) of the harmful light HL to the adjacent G emission unit 26G. In the example illustrated in FIG. 8, the harmful light HL is the green fluorescence. The wavelength range of the harmful light HL partially overlaps the wavelength range of the light which passes through the filter 34G of the G emission unit 26G. However, the light shielding section 51 blocks the transmission of the harmful light HL to the G emission unit 26G from the B emission unit 26B in which the harmful light HL occurs. Thus, the harmful light HL is not released from the G emission unit 26G. As a result, the harmful light HL is not imaged by the image sensor 22 and therefore does not appear in the fluorescent image taken. The fluorescent image has excellent contrast without noise.

In this example, the light shielding section 51 composed of the plurality of through holes 51a allows high flexibility in the installation of wiring. The area of one through hole 51a is less than or equal to the area of the LED 33, so that the reduction in the strength and the rigidity of the circuit board 32 is suppressed. At least one through hole 51a is disposed in one linear path of the harmful light HL traveling between the adjacent mounting areas 38, so that high light shielding effect is achieved. The light shielding sections 51 are arranged around the mounting area 38, preventing both the linear and diffracted harmful light HL from entering the mounting area 38.

Figure 16:
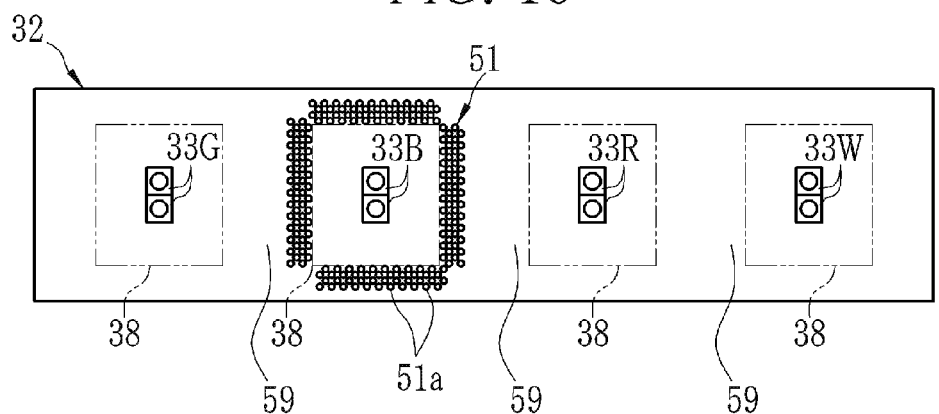
FIG. 16 is an explanatory view illustrating an example in which the light shielding sections are provided around the mounting area of the emission unit in which the harmful light occurs.
Figure 17:
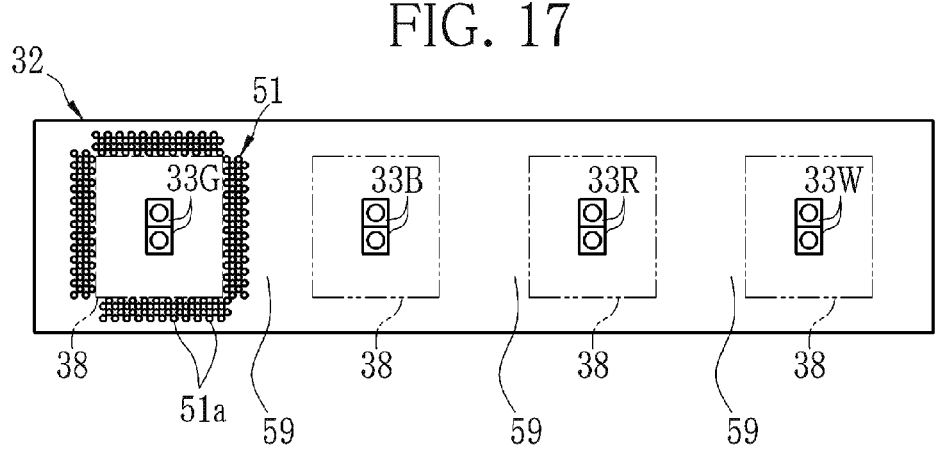
FIG. 17 is an explanatory view illustrating an example in which the light shielding sections are provided around the mounting area into which the harmful light is supposed to enter.

The above embodiment is described by way of example and may be modified in various ways, which will be described below. In the above embodiment, the light shielding sections 51 are provided around the mounting area 38 of each of the emission units 26B, 26G, 26R, and 26W, which share the single circuit board 32, by way of example. The light shielding sections 51 may not be provided to all of the mounting areas 38. In the case where only the green harmful light HL occurs in the B emission unit 26B as described above, and there is no other harmful light HL (the harmful light HL of a different color or the harmful light occurred in the emission unit 26 of a different color), the light shielding sections 51 may be provided around at least one of the mounting areas 38 of the B emission unit 26B and the G emission unit 26G as illustrated in examples in FIGS. 15 to 17.

Figure 15:
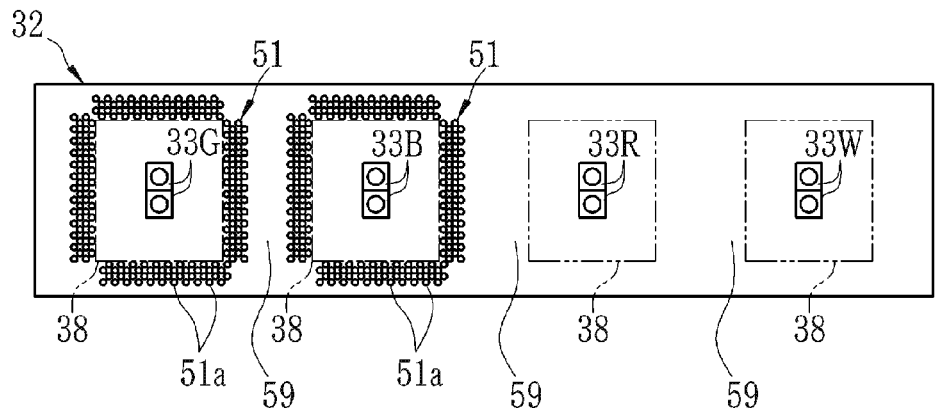
FIG. 15 is an explanatory view of an example in which the light shielding sections are provided around a mounting area of an emission unit in which the harmful light occurs and a mounting area of an emission unit into which entrance of the harmful light is avoided.

In the example illustrated in FIG. 15, the light shielding sections 51 are provided around the mounting area 38 of each of the B emission unit 26B and the G emission unit 26G. In the example illustrated in FIG. 16, the light shielding section 51 is provided around the mounting area 38 of the B emission unit 26B only. In the example illustrated in FIG. 17, the light shielding sections 51 are provided around the mounting area 38 of the G emission unit 26G only. In other words, in the example illustrated in FIG. 16, the light shielding sections 51 prevent the harmful light HL from being transmitted to the outside of the location of occurrence of the harmful light HL. In the example illustrated in FIG. 17, the entrance of the harmful light HL transmitted from the location of occurrence is blocked.

Figure 18:
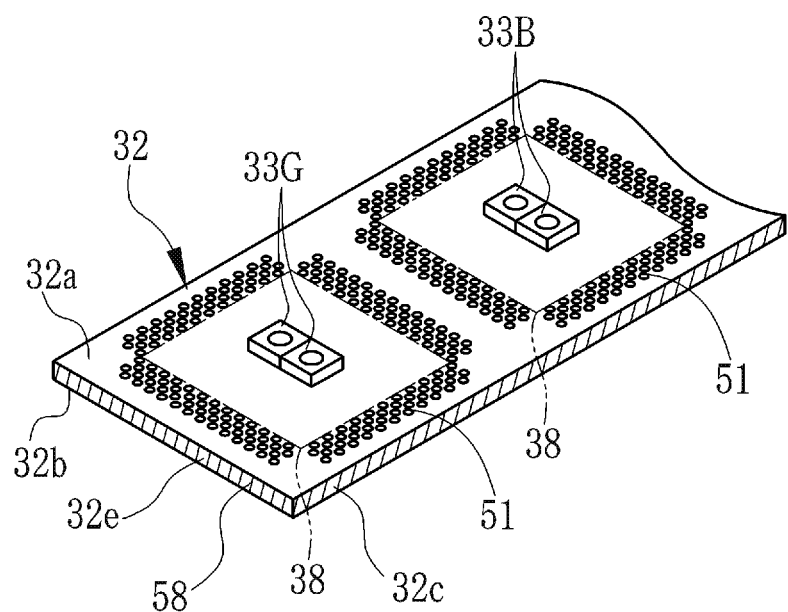
FIG. 18 is an explanatory view illustrating an example in which a light absorption coating is applied to a side edge face of the circuit board.

As illustrated in FIG. 18, a light absorption coating 58, which is illustrated with a hatch pattern, may be applied to a side edge face 32e extending in the thickness direction of the circuit board 32. The light absorption coating 58 has light absorption property. The side edge face 32e is an interface with air. When the harmful light HL transmitted inside the circuit board 32 enters the side edge face 32e, a part of the harmful light HL passes through the side edge face 32e and is released to the outside, but the totally reflected harmful light HL changes its light path and stays within the circuit board 32. The harmful light HL stayed within the circuit board 32 may enter the mounting area 38. By applying the light absorption coating 58 to the side edge face 32e, the side edge face 32e absorbs the harmful light HL entered thereto. Thus, the light absorption coating 58 prevents the harmful light HL from entering the mounting area 38. For example, carbon black or a black dye is used as the light absorption coating 58.

A plate-like light shielding member (see a numeral 72 in FIG. 26 by way of example) may be provided to the back surface 32b side of the circuit board 32. The light shielding member has light absorption property and prevents leakage of the harmful light HL through the back surface 32b side of the circuit board 32. Note that the thermal conductive sheet 41 (see FIGS. 5 and 11) described in the first embodiment may also serve as the light shielding member. For example, in a case where the thermal conductive sheet 41 is formed from a carbon material with high thermal conductivity, the thermal conductive sheet 41 has black color and exhibits light absorption property. Thus, the thermal conductive sheet 41 also serves as the light shielding member.

The through hole 51a has a circular plan shape by way of example. The word "circular" includes "perfectly circular", "approximately circular", and "oval". The through hole 51a may have a polygonal (e.g. triangular or rectangular) shape. However, the circular shape is preferred because the angles of the polygonal shape may be disadvantageous in terms of the strength and the rigidity of the circuit board 32. A perfectly circular shape is more preferred than an oval shape in terms of easiness in processing.

(Second Embodiment)

Figure 19:
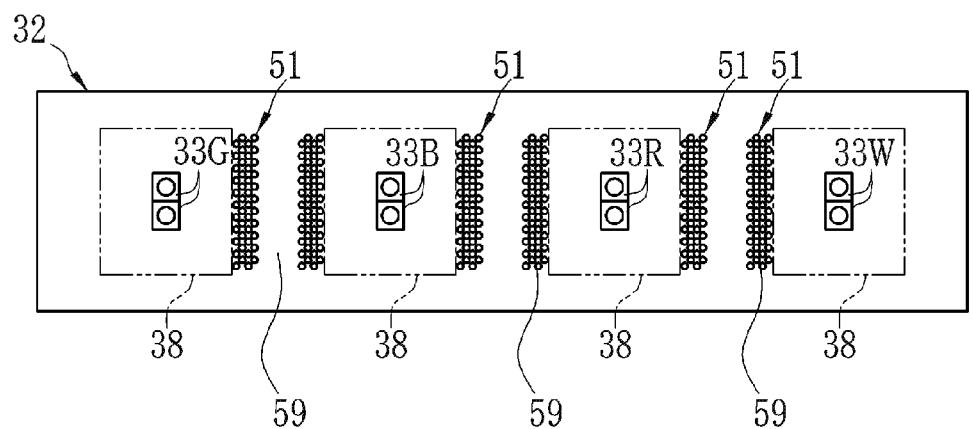
FIG. 19 is an explanatory view illustrating an example in which two light shielding sections are provided in a boundary region between the adjacent mounting areas.
Figure 20:
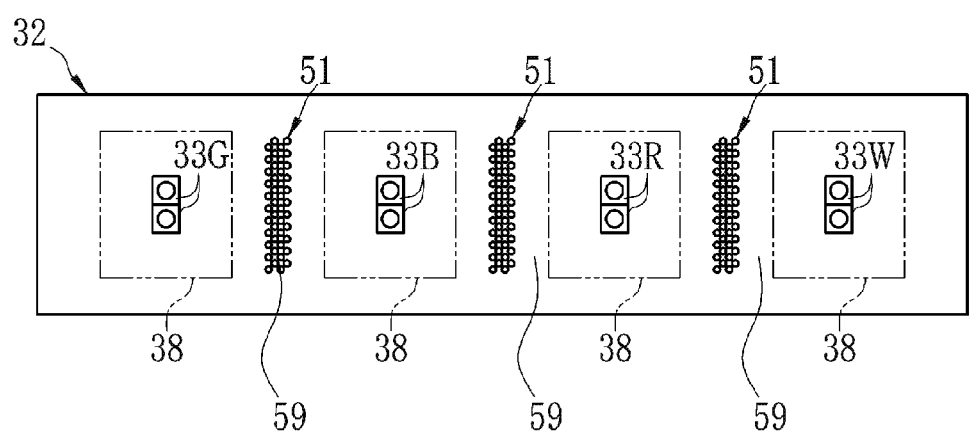
FIG. 20 is an explanatory view illustrating an example in which one light shielding section is provided in the boundary region between the adjacent mounting areas.

A second embodiment illustrated in FIGS. 19 and 20 describes modifications of the arrangement of the light shielding sections 51 of the first embodiment. In the first embodiment, the light shielding sections 51 are provided to surround the mounting area 38, more specifically, to the positions which correspond to the four respective sides of the mounting area 38. Alternatively, the light shielding section 51 may be provided only in the boundary region 59 between the adjacent mounting areas 38 as described in the second embodiment.

In the example illustrated in FIG. 19, the light shielding section 51 is provided to each mounting area 38 but only to the sides facing the adjacent mounting areas. In FIG. 19, each boundary region 59 is provided with the two light shielding sections 51, by way of example. The example illustrated in FIG. 20 differs from that illustrated in FIG. 19. In FIG. 20, each boundary region 59 is provided with one light shielding section 51.

(Third Embodiment)

Figure 21:
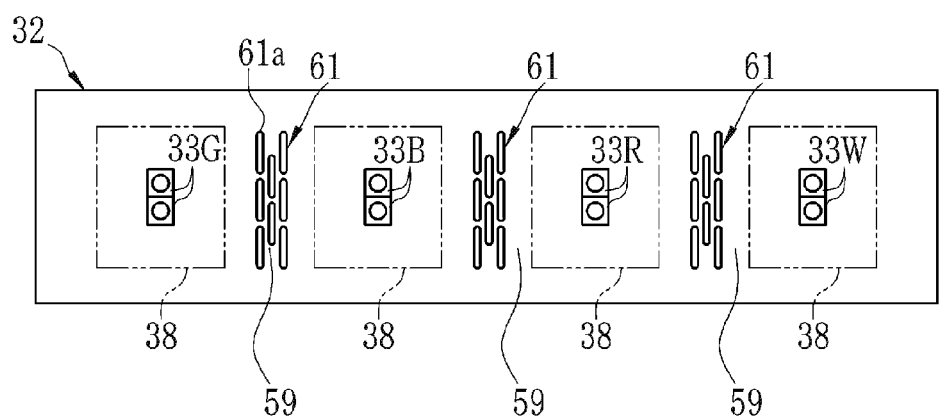
FIG. 21 is an explanatory view illustrating an example in which each of the light shielding sections is composed of long thin through holes.
Figure 22:
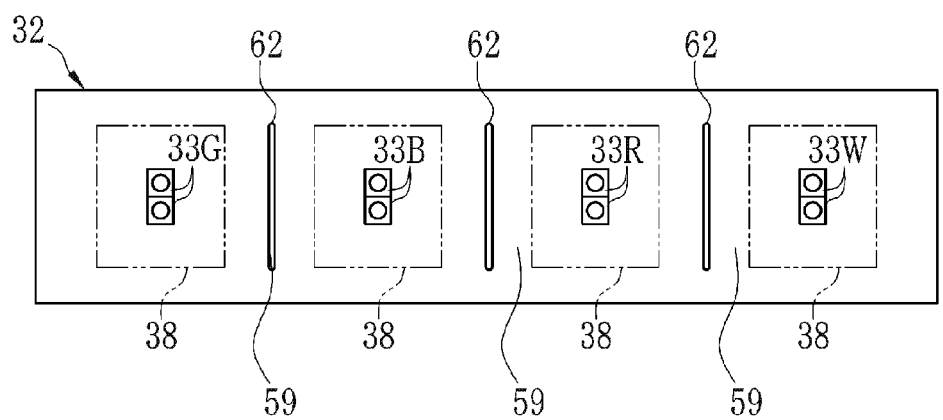
FIG. 22 is an explanatory view illustrating an example in which each of the light shielding sections is composed of one long thin through hole.

A third embodiment illustrated in FIGS. 21 and 22 describes examples in which long thin through holes are used. In FIG. 21, a light shielding section 61 is composed of two or more through holes 61a. Each through hole 61a is a long thin hole. The through holes 61a are in a staggered arrangement. A length of the through hole 61a and an arrangement pitch of the through holes 61a are set such that at least one through hole 61a is placed in a linear path of the harmful light HL traveling between the adjacent mounting areas 38, in a manner similar to the first embodiment illustrated in FIG. 13. A light shielding effect similar to that in the first embodiment is achieved in the example illustrated in FIG. 21. However, the circular through holes 51a with the small diameter described in the first embodiment are more advantageous than the long thin through holes 61a in terms of the strength and the rigidity of the circuit board 32. Also, the circular through holes 51a, which create more spaces than the long thin through holes 61a do, are advantageous in terms of the flexibility in installing the wiring as illustrated in FIG. 12.

In the example illustrated in FIG. 22, the light shielding section is composed of one through hole 62. The through hole 62 is a long thin hole. Since the light shielding section serves to prevent the transmission of the harmful light HL between the adjacent mounting areas 38, the length of the light shielding section is determined in accordance with the size of the mounting area 38. The length of the through hole 62 is substantially the same as the width (the length of one side) of the mounting area 38. Thereby, the through hole 62 surely prevents the transmission of the harmful light HL between the adjacent mounting areas 38. Thus, the light shielding effect similar to that in the example illustrated in FIG. 21 is achieved. The harmful light HL traveling linearly between the mounting areas 38 is blocked by the light shielding section even if the light shielding section is composed of the single long through hole 62, so long as the length of the through hole 62 is substantially the same as the width of the mounting area 38. Shorter the length of the through hole, the better to ensure the strength and the rigidity of the circuit board 32. In consideration of the balance between the strength of the circuit board 32 and the light shielding effect, the upper limit of the length of the through hole is preferred to be less than or equal to the width of the mounting area 38.

In the case where the through hole 62 is one long through hole, the length of the long through hole 62 is longer than that in the example illustrated in FIG. 21. The long through hole is less preferred than the through holes in the example illustrated in FIG. 21 in terms of the strength and the rigidity of the circuit board 32 and the flexibility in installing the wiring. Ina case where the strength and the rigidity of the circuit board 32 and the flexibility in installing the wiring are important factors, the example illustrated in FIG. 21 and the first embodiment are preferred.

(Fourth Embodiment)

Figure 23:
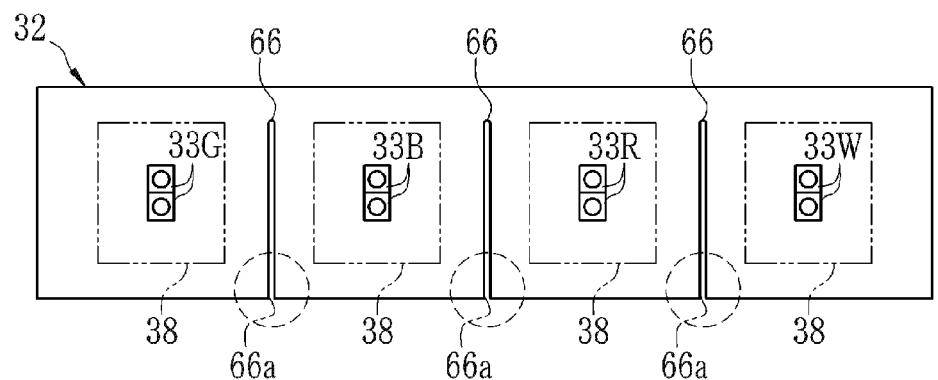
FIG. 23 is an explanatory view illustrating an example in which each of the light shielding sections is composed of a slit with an open end.

A fourth embodiment illustrated in FIG. 23 is an example in which a through hole, which constitutes the light shielding section, is a long thin slit (or cutout) 66 with an open end 66a. The light shielding effect of blocking the harmful light HL is also achieved by the slit 66. However, in a case where the through hole is the slit 66 with the open end 66a, the wiring cannot be installed in an area around the open end 66a encircled with dotted lines in FIG. 23. This example is less preferred than the example illustrated in FIG. 22 in terms of the flexibility in installing the wiring. One of the ends of the slit 66 is the open end 66a, which is furthermore disadvantageous in terms of the strength and the rigidity of the circuit board 32. In the case where the strength of the circuit board 32 is an important factor, it is preferred that the through hole does not have the open end, as described in the first to third embodiments. More specifically, an inner wall of the through hole is preferred to have a closed curved cross-section, like the through holes 51a, 61a, and 62.

(Fifth Embodiment)

Figure 24:
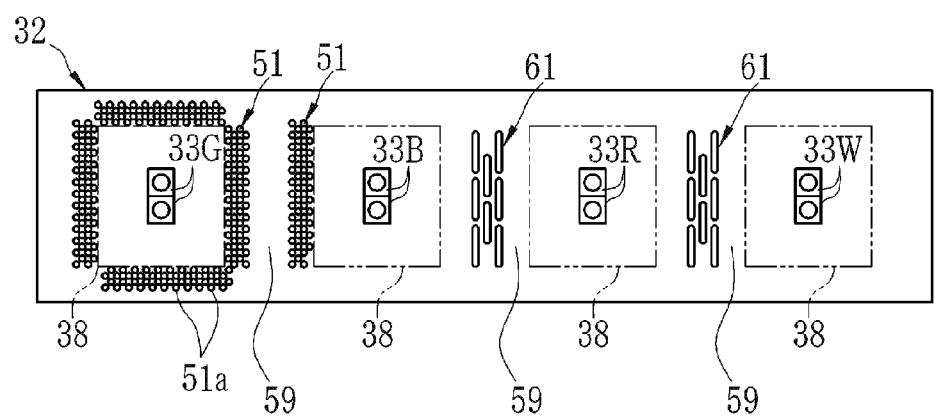
FIG. 24 is an explanatory view illustrating an example in which the through holes of various shapes are used.

In a fifth embodiment, the through holes of the first to fourth embodiments may be used in combination. In FIG. 24, the through holes of the first to third embodiments are used in combination by way of example. A different combination of the through holes may be used.

(Sixth Embodiment)

Figure 25:
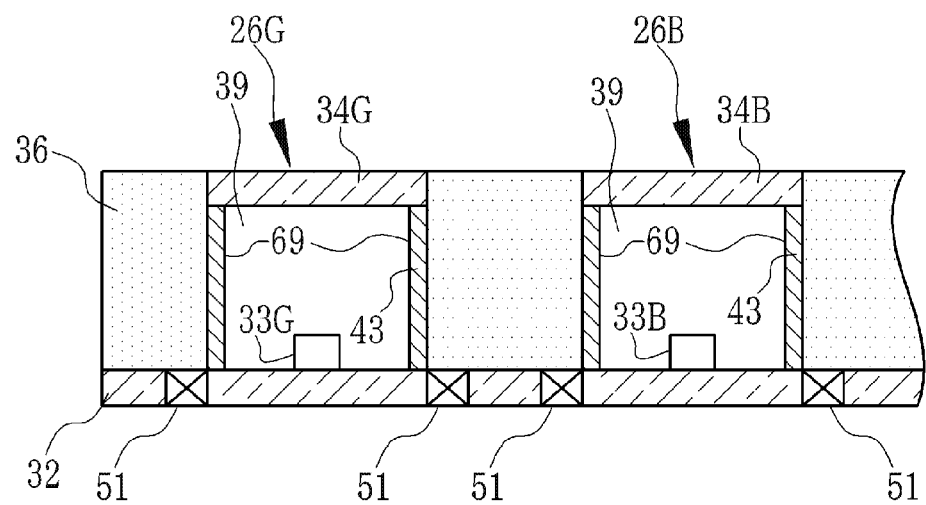
FIG. 25 is an explanatory view illustrating an example in which sleeves are provided in a mounting space in the emission unit.

A sixth embodiment illustrated in FIG. 25 describes an example in which sleeves 69 are provided inside the mounting space 39 in each emission unit 26. The shape and the size of the sleeve 69 correspond to the shape and the area of the mounting area 38 and the height of the mounting space 39. The sleeve 69 functions as a positioning member for positioning the filter 34 in the height direction, for example. The material of the sleeve 69 may be hard rubber, plastic, or metal, for example. It is preferred that the sleeve 69 is made from a material which does not transmit light. The sleeve 69 fits in the clearance between the filter 34 and the window frame 42 of the window frame block 36. The sleeve 69, which does not transmit light, prevents light from leaking through the clearance between the filter 34 and the window frame 42.

(Seventh Embodiment)

Figure 26:
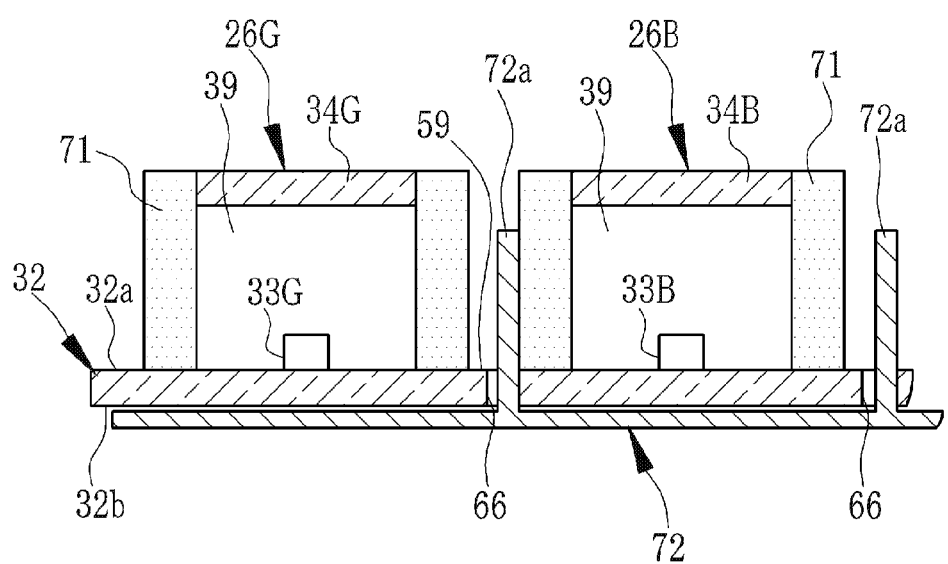
FIG. 26 is an explanatory view illustrating an example in which a rib is provided between the adjacent emission units.

A seventh embodiment illustrated in FIG. 26 is an example in which separate window frame blocks 71 are provided to the respective emission units 26, instead of the window frame block 36 shared by the emission units 26. Thus, the window frame block may not necessarily be shared by the emission units 26. In the seventh embodiment, the slit 66 illustrated in FIG. 23 is provided as the through hole for blocking the harmful light HL in the circuit board 32. The light shielding member 72, which prevents light leakage to the outside of the light source unit 19 through the back surface 32b, is disposed on the back surface 32b side of the circuit board 32. The light shielding member 72 is provided with a rib 72a, which is inserted through the slit 66 and disposed between the emission units 26. The slit 66 is disposed between the emission units 26B and 26G. The slit 66 prevents the light from being transmitted between the emission units 26B and 26G through the circuit board 32. The rib 72a ensures preventing the light leakage between the emission units 26B and 26G.

(Eighth Embodiment)

Figure 27:
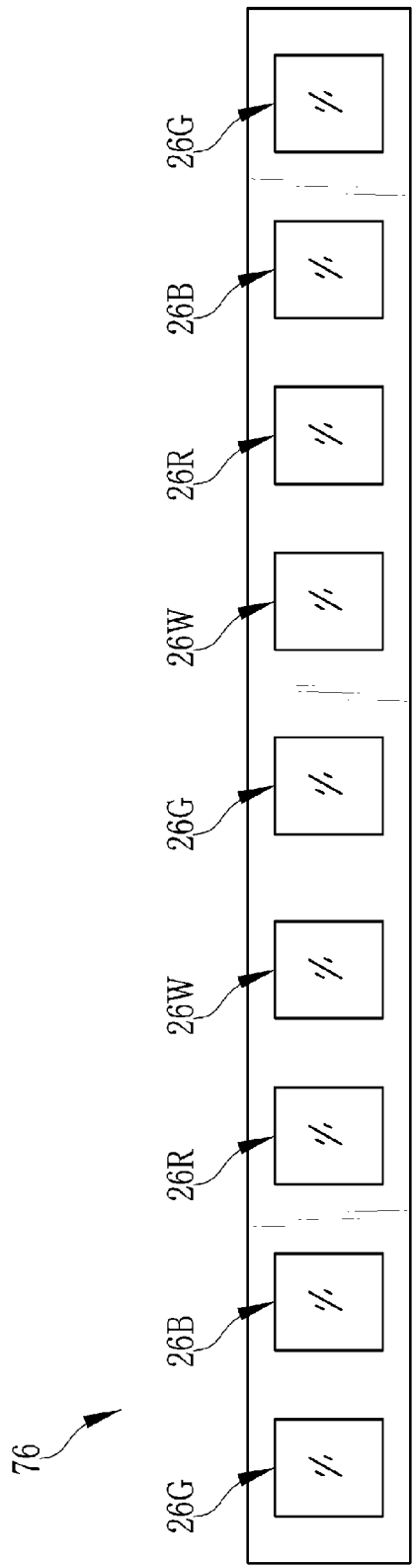
FIG. 27 is an explanatory view illustrating an example of combining various types of emission units.

A light source unit 76 according to an eighth embodiment comprises two or more emission units (26G, 26B, 26R, and 26W) for the light of each color as illustrated in FIG. 27. For example, the light source unit 76 is provided with the three emission units 26G, and two each of the emission units 26B, 26R, and 26W. The emission unit 26G is disposed in the middle between the sets of the emission units each composed of the emission units 26G, 26B, 26R, and 26W. The arrangement and the number of the emission units 26G, 26B, 26R, and 26W may be changed as appropriate. The combination of the colors of the emission units is described by way of example. For example, the combination of the emission units 26G and 26B of only two colors may be used. Light of a different color may be used, for example, UV (Ultra-Violet) or infrared light.

The first to seventh embodiments describe the light source unit in which the single circuit board 32 is shared by the four types of emission units 26 different in color. The eighth embodiment describes the light source unit in which the single circuit board 32 is shared by the nine types of the emission units 26. Note that the present invention is applicable to the light source unit in which the single circuit board 32 is shared by at least two or more types of the emission units 26. Note that the present invention relates to the light source unit capable of applying different types (different colors) of excitation light such as the one having the B emission unit 26B and the G emission unit 26G. The present invention does not include the light source unit having only the emission units 26 of the same type (e.g. the light source unit having only the B emission units 26B). In the case where the emission units of the same type are used, it is unnecessary to prevent the harmful light HL occurred in one of the emission units from entering another emission unit.

As illustrated in FIG. 2, two or more light source units 19, in each of which the different types of the emission units 26 share the single circuit board 32, may be used. Two or more types of light source units which differ from each other in combination of colors of the emission units 26 may be provided. For example, a light source unit in which the B emission unit 26B and the G emission unit 26G share the single circuit board 32 and a light source unit in which the R emission unit 26R and the W emission unit 26W share the single circuit board 32 may be used.

The different types of emission units 26 are arranged one-dimensionally in the light source unit 19 byway of example. The different types of emission units 26 may be arranged two-dimensionally.

In the case where the emission unit in which the harmful light HL occurs is located next to the emission unit into which the entrance of the harmful light HL needs to be avoided, like the B emission unit 26B and the G emission unit 26G described in the above embodiments, the light shielding section is disposed in the boundary region between the adjacent emission units. The light shielding section may not necessarily be disposed in the boundary region of the adjacent emission units. For example, there may be cases where the R emission unit 26R is disposed between the B emission unit 26B in which the harmful light HL occurs and the G emission unit 26G into which the entrance of the harmful light HL needs to be blocked. In this case, the light shielding section 51 may be provided between the B emission unit 26B and the R emission unit 26R, or between the G emission unit 26G and the R emission unit 26R.

In the above embodiments, the different types of the light emitting elements with the different emission wavelength ranges are used for the different types of the emission units byway of example. The light emitting elements of the same type may be used as long as the different types of the emission units are capable of applying different types of excitation light. For example, the light emitting elements of the same type which emit white light may used for all of the different types of the emission units. With the use of different excitation light filters for the respective emission units, the different types of the emission units generate different types of excitation light. The LED is used as the light emitting element by way of example. A semiconductor light source such as a laser diode or an organic EL (Electro-Luminescence) device may be used instead.

A printed circuit board, in which the wiring pattern is printed on the glass epoxy substrate, is described as the circuit board by way of example. The present invention is applicable to any circuit board, for example, a flexible circuit board, as long as the circuit board has a substrate with light transmitting property. An excitation light cutting filter for cutting the excitation light may be used as necessary to prevent the excitation light from entering the image sensor 22.

The monochrome image sensor is used as the image sensor 22 by way of example. Alternatively, a color image sensor with color microfilters, which are provided to the respective pixels, may be used. The color microfilters may be of a primary color system of blue (B), green (G), and red (R) or a complementary color system of yellow (Y), magenta (M) and cyan (C). In the case where the color image sensor is used, the color image sensor may be used in combination with the filter unit 25 that cuts the light other than the fluorescence SFL to be detected. The color image sensor may just use the color microfilters without the filter unit 25.

Various changes and modifications are possible in the present invention and may be understood to be within the present invention.

What is claimed is:

1. A fluorescence imaging apparatus for exciting a fluorescent substance contained in a sample and detecting excited fluorescence and taking a fluorescence image, the fluorescence imaging apparatus comprising:
   a camera section; and
   a light source unit for applying different types of excitation light to the sample for the purpose of exciting the fluorescent substance, the different types of the excitation light having different wavelength ranges, the light source unit comprising:
   different types of emission units having a plurality of light emitting elements and different types of excitation light filters, the each emission unit having at least one of the light emitting elements and one of the excitation light filters, the each excitation light filter being disposed in front of the at least one light emitting element in a direction of applying light and limiting a wavelength range of the light from the at least one light emitting element and thereby the different types of the excitation light being applied;
   a circuit board having a light-transmitting substrate, the light emitting elements being mounted on the circuit board, the different types of the emission units being arranged in one or two dimensions over the circuit board and sharing the circuit board, mounting areas on which the light emitting elements are mounted being provided on the circuit board;
   a light shielding section composed of through holes formed through the circuit board so as to prevent a light occurring due to the circuit board from being transmitted from one of the emission units through the circuit board and entering the adjacent emission unit, the one of the emission units and the adjacent emission unit differing in type; and
   a window frame block provided on one surface of the circuit board to contact to the surface, and defining mounting spaces each of which is formed between one of the mounting areas and one of the excitation light filters in the each emission unit, the window frame block including a wall defining a boundary between adjacent mounting spaces to prevent light leakage into an adjacent mounting space, the window frame block and the excitation light filters attached thereto composing emission windows of the different types of emission units,
   wherein the light shielding section is disposed in a boundary region between the adjacent emission units of the different types of the emission units.

2. The fluorescence imaging apparatus according to claim 1, wherein an inner wall of the through hole has a closed curved cross-section.

3. The fluorescence imaging apparatus according to claim 2, wherein the light shielding section is composed of a group of the through holes.

4. The fluorescence imaging apparatus according to claim 3, wherein the at least one light shielding section is disposed between the different types of the emission units.

5. The fluorescence imaging apparatus according to claim 4, wherein the emission unit has a mounting area on which the light emitting element is mounted, and the mounting area is provided on the circuit board and faces the excitation light filter, and the light shielding sections are arranged around the mounting area.

6. The fluorescence imaging apparatus according to claim 3, wherein the emission unit has a mounting area on which the light emitting element is mounted, and the mounting area is provided on the circuit board and faces the excitation light filter, and a length of the through hole is less than or equal to a width of the mounting area.

7. The fluorescence imaging apparatus according to claim 6, wherein an area of the through hole is less than or equal to an area of the light emitting element.

8. The fluorescence imaging apparatus according to claim 3, wherein a coating which reflects or absorbs the light is applied to the inner wall of the through hole.

9. The fluorescence imaging apparatus according to claim 8, wherein the coating is conductive plating.

10. The fluorescence imaging apparatus according to claim 3, wherein a shape of the through hole is any of polygon, circle, and oval shape.

11. The fluorescence imaging apparatus according to claim 3, wherein the light emitting element is an LED.

12. The fluorescence imaging apparatus according to claim 3, wherein the through hole allows insertion of a terminal of a component mounted on the circuit board.

13. The fluorescence imaging apparatus according to claim 3, wherein the at least one through hole is disposed in a linear path of the light occurring in one of the different types of the emission units and traveling linearly toward the another emission unit.

14. The fluorescence imaging apparatus according to claim 13, wherein the through holes are in a staggered arrangement with respect to each other.

15. The fluorescence imaging apparatus according to claim 1, wherein a material of the circuit board is glass epoxy.

16. The fluorescence imaging apparatus according to claim 15, wherein the excitation light filters include a green excitation light filter for generating green excitation light having a wavelength range of a green region.

17. A light source unit used in a fluorescence imaging apparatus for exciting a fluorescent substance contained in a sample and detecting excited fluorescence and taking a fluorescent image, the light source unit applying different types of excitation light to the sample for the purpose of exciting the fluorescent substance, the different types of the excitation light having different wavelength ranges, the light source unit comprising:

different types of emission units having a plurality of light emitting elements and different types of excitation light filters, the each emission unit having at least one of the light emitting elements and one of the excitation light filters, the each excitation light filter being disposed in front of the at least one light emitting elements in a direction of applying light and limiting a wavelength range of the light from the at least one light emitting element and thereby the different types of the excitation light being applied;

a circuit board having a light-transmitting substrate, the light emitting elements being mounted on the circuit board, the different types of the emission units being arranged in one or two dimensions over the circuit board and sharing the circuit board, mounting areas on which the light emitting elements are mounted being provided on the circuit board;

a light shielding section composed of through holes formed through the circuit board so as to prevent a light occurring due to the circuit board from being transmitted from one of the emission units through the circuit board and entering the adjacent emission unit, the one of the emission units and the adjacent emission unit differing in type; and a window frame block provided on one surface of the circuit board to contact to the surface, and defining mounting spaces each of which is formed between one of the mounting areas and one of the excitation light filters in the each emission unit, the window frame block including a wall defining a boundary between adjacent mounting spaces to prevent light leakage into an adjacent mounting space, the window frame block and the excitation light filters attached thereto composing emission windows of the different types of emission units, wherein the light shielding section is disposed in a boundary region between the adjacent emission units of the different types of the emission units.

18. The fluorescence imaging apparatus according to claim 1, wherein the window frame block comprises an elastic material.

19. The fluorescence imaging apparatus according to claim 1, further comprising a light shielding member having a light absorption property and disposed at a position opposed to the mounting areas on a back surface side of the circuit board.

20. The fluorescence imaging apparatus according to claim 19, wherein the light shielding member includes at least one rib disposed between the emission units.

21. The fluorescence imaging apparatus according to claim 1, further comprising a sleeve having a light shielding property, on an inner surface of the wall and having a shape and a size corresponding to the mounting space.

* * * * *